(12) United States Patent
Dervieux

(10) Patent No.: US 7,695,908 B2
(45) Date of Patent: Apr. 13, 2010

(54) METHODS FOR PREDICTING METHOTREXATE POLYGLUTAMATE LEVELS USING PHARMACOGENETICS

(75) Inventor: Thierry Dervieux, San Diego, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 854 days.

(21) Appl. No.: 11/152,128

(22) Filed: Jun. 13, 2005

(65) Prior Publication Data

US 2006/0057609 A1 Mar. 16, 2006

Related U.S. Application Data

(60) Provisional application No. 60/580,141, filed on Jun. 15, 2004.

(51) Int. Cl.
*C12Q 1/68* (2006.01)
(52) U.S. Cl. .......................................................... 435/6
(58) Field of Classification Search ...................... None
See application file for complete search history.

(56) References Cited

U.S. PATENT DOCUMENTS

| | | | |
|---|---|---|---|
| 2004/0101834 A1 | 5/2004 | Assaraf et al. | |
| 2005/0112627 A1* | 5/2005 | Dervieux et al. | 435/6 |
| 2006/0008811 A1 | 1/2006 | Evans et al. | |

FOREIGN PATENT DOCUMENTS

WO 2005022118 A 3/2005

OTHER PUBLICATIONS

Halushka, et al. Nature Genetics, 1999; 22:239-247.*
Dervieux, et al. Pharmacogenetics 2004; 14:733-739.*
Whetstine, et al. Clinical Cancer Research, Nov. 2001; 7:3416-3422.*
Yao, et al. Proc. Natl. Acad. Sci., Sep. 1996; 93:10134-10138.*
Rosenthal, et al. J Clin Invest. Dec. 1978;62(6):1181-6.*
Chango et al. (Molecular Genetics and Metabolism 2000 vol. 70 p. 310).*
Cole et al. (Cancer Research 2001 vol. 61 p. 4599).*
Buchholz et al. (European Journal of Cancer 1996 vol. 32A p. 2101).*
Kager et al. (The journal of clinical investigation 2005 vol. 115 p. 110).*
Ranganathan et al. (Arthritis and rheumatism 2006 vol. 54 p. 1366).*
Dervieux et al. Arthritis and Rheumatism vol. 54 p. 3095.*
Masson; Eric; Accumulation of Methotrexate Polyglutamates in Lymphoblasts is a Determinant of Antileukemic Effects In Vivo; J. Clin. Invest.; Jan. 1996; vol. 97, No. 1; 0021-9738/96/01/0073/08.

Laverdiere, Caroline; Polymorphism $G_{80}A$ in the reduced folate carrier gene and its relationship to methotrexate plasma levels and outcome of childhood acute lymphoblastic leukemia; Blood, Nov. 15, 2002; vol. 100, No. 10; 3832-3834.
Ranganathan, P.; Will pharmacogenetics allow better prediction of methotrexate toxicity and efficacy in patients with rheumatoid arthritis; Annals of the Rheumatic Diseases; 2003; 62:4-9.
Abalo Chango et al., A Polymorphism (80G->A) in the Reduced Folate Carrier Gene and its Associations with Folate Status and Homocysteinemia. Molecular Genetics and Metabolism 70, 310-315 (2000).
Karen J. Chave et al., Identification of single nucleotide polymorphisms in the human γ-glutamyl hydrolase gene and characterization of promoter polymorphisms. Science @ Direct, Gene 319, 167-175 (2003).
Isabelle Morin et al., Evaluation of genetic variants in the reduced folate carrier and in glutamate carboxypeptidase II for spina bifida risk. Science @ Direct, Molecular Genetics and Metabolism 79, 197-200 (2003).
Gary M. Shaw et al., Maternal Periconceptional Vitamin Use, Genetic Variation of Infant Reduced Folate Carrier (A80G), and Risk of Spina Bifida. American Journal of Medical Genetics 108:1-06 (2002).
Supplementary European Search Report dated Dec. 4, 2008; EP Patent Application No. 05762644.2; based on PCT/US2005020957.
Longo G S A et al., "Gamma-glutamylhydrolase and folylpolyglutmate synthetase activities predict polyglutamylation of methotrexate in acute leukemias" Oncology Research, vol. 9, pp. 259-263, Jan. 1, 1997.
Angelis-Stoforidis P et al., "Methotrexate polyglutamate levels in circulating erythrocytes and polymorphs correlate with clinical efficacy in rheumatoid arthritis," Clinical and Experimental Rheumatology, vol. 17, pp. 313-320, Jan. 1, 1999.
Chen, Qing et al., "A substrate specific functional polymorphism of human gamma-glutamyl hydrolase alters catalytic activity and methotrexate polyglutamate accumulation in acute lymphoblastic leukaemia cells," Pharmacogenetics, vol. 14, No. 8, pp. 557-567, Aug. 2004.

* cited by examiner

*Primary Examiner*—Sarae Bausch
*Assistant Examiner*—Katherine Salmon
(74) *Attorney, Agent, or Firm*—Cooley Godward Kronish LLP

(57) ABSTRACT

The present invention provides methods for determining a level of methotrexate polyglutamates (MTXPGs) in an individual undergoing methotrexate (MTX) therapy and for optimizing dose efficacy of MTX therapy in an individual by genotyping the individual at a polymorphic site in at least one folate pathway gene (e.g., a reduced folate carrier (RFC-1) gene, a gamma glutamyl hydrolase (GGH) gene, etc.). Methods are also provided for determining a level of MTXPGs in an individual undergoing MTX therapy and for optimizing dose efficacy of MTX therapy in an individual by generating a pharmacogenetic index based upon the genotype of the individual at a polymorphic site in an RFC-1 gene and/or a GGH gene.

20 Claims, 4 Drawing Sheets

Methotrexate

Methotrexate polyglutamates

N=2 to 7

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Forward PCR Primer

<400> SEQUENCE: 1
agtgtcacct tcgtcccctc                                                  20

<210> SEQ ID NO 2
<211> LENGTH: 18
<212> TYPE: DNA
<213> ORGANISM: Artificial
<220> FEATURE:
<223> OTHER INFORMATION: Reverse PCR Primer

<400> SEQUENCE: 2
ctcccgcgtg aagttctt                                                    18

<210> SEQ ID NO 3
<211> LENGTH: 20
<212> TYPE: DNA
<213> ORGANISM: Artificial
<220> FEATURE:
<223> OTHER INFORMATION: Forward PCR Primer

<400> SEQUENCE: 3
cgctgcctgg ttaccaaact                                                  20

<210> SEQ ID NO 4
<211> LENGTH: 23
<212> TYPE: DNA
<213> ORGANISM: Artificial
<220> FEATURE:
<223> OTHER INFORMATION: Reverse PCR Primer

<400> SEQUENCE: 4
tgttacgtcg atgtggactt cag                                              23
```

METHODS FOR PREDICTING METHOTREXATE POLYGLUTAMATE LEVELS USING PHARMACOGENETICS

CROSS-REFERENCES TO RELATED APPLICATIONS

The present application claims priority to U.S. Provisional Application No. 60/580,141, filed Jun. 15, 2004, which is herein incorporated by reference in its entirety for all purposes.

BACKGROUND OF THE INVENTION

Folate (folic acid) is a vitamin that is essential for the life-sustaining processes of DNA synthesis, replication, and repair. Folate is also important for protein biosynthesis, another process that is central to cell viability. The pteridine compound, methotrexate (MTX), is structurally similar to folate and as a result can bind to the active sites of a number of enzymes that normally use folate as a coenzyme for biosynthesis of purine and pyrimidine nucleotide precursors of DNA and for interconversion of amino acids during protein biosynthesis. Despite its structural similarity to folic acid, methotrexate cannot be used as a cofactor by enzymes that require folate, and instead competes with the folate cofactor for enzyme binding sites, thereby inhibiting protein and DNA biosynthesis and, hence, cell division.

The ability of the folate antagonist methotrexate to inhibit cell division has been exploited in the treatment of a number of diseases and conditions that are characterized by rapid or aberrant cell growth. For example, methotrexate is currently one of the most widely prescribed drugs for the treatment of rheumatoid arthritis, psoriasis, and cancer (Weinblatt et al., *Eng. J. Med.*, 312:818-822 (1985); Kremer and Lee, *Arthritis Rheum.*, 29:822-831 (1986)). Although methotrexate is among the best tolerated of the disease-modifying anti-rheumatic drugs, a major drawback of methotrexate therapy is a troublesome inter-patient variability in the clinical response and an unpredictable appearance of side-effects including gastrointestinal disturbances, alopecia, elevation of liver enzymes, and bone marrow suppression (Weinblatt et al., *Arthritis Rheum.*, 37:1492-1498 (1994); Walker et al., *Arthritis Rheum.*, 36:329-335 (1993)). Several studies in well-controlled clinical trials have demonstrated that methotrexate is effective at decreasing functional disability, with the maximum effect occurring after about six months of therapy. However, recent findings from retrospective studies on a large cohort of patients with rheumatoid arthritis have suggested that methotrexate dosage may be suboptimal in some patients (Ortendahl et al., *J. Rheumatol.*, 29:2084-2091 (2002)). Thus, the lack of efficient therapeutic drug monitoring of methotrexate therapy and difficulty of rapidly individualizing methotrexate dose-maximizing response hampers effective patient treatment.

Methotrexate enters cells through the reduced folate carrier (RFC-1) and is intracellularly activated by folylpolyglutamate synthase to methotrexate polyglutamates (MTXPGs) (Chabner et al., *J. Clin. Invest.*, 76:907-912 (1985)). The γ-linked sequential addition of glutamic acid residues enhances intracellular retention of methotrexate (Allegra et al., *Proc. Natl. Acad. Sci. USA*, 82:4881-4885 (1985)). The polyglutamation process is in competition with deconjugation by gamma glutamyl hydrolase (GGH) (Rhee et al., *Mol. Pharmacol.*, 53:1040-1046 (1998); Yao et al., *Proc. Natl. Acad. Sci. USA*, 93:10134-10138 (1996); Panetta et al., *Clin. Cancer Res.*, 8:2423-2429 (2002)), a lysosomal enzyme having high affinity towards long chain polyglutamates. (Masson et al., *J. Clin. Invest.*, 97:73-80 (1996)).

The accumulation of MTXPGs is critical to the pharmacological effects of methotrexate. In vivo, the concentration of MTXPGs in lymphoblasts and erythrocytes appear to correlate with the therapeutic response to methotrexate in patients with leukemia (Dervieux et al., *Blood*, 100:1240-1247 (2002); Dervieux et al., *Arthritis Rheum.*, in press, (2004)) or rheumatoid arthritis (Angelis-Stoforidis et al., *Clin. Exp. Rheumatol.*, 17:313-320 (1999); Allegra et al., *Proc. Natl. Acad. Sci. USA*, 82:4881-4885 (1985)). Polyglutamation of methotrexate is thought to promote the sustained inhibition of de novo purine synthesis by 5-aminoimidazole carboxamideribonucleotide transformylase (ATIC) (Dervieux et al., *Blood*, 100:1240-1247 (2002); Allegra et al., supra, (1985)), thereby promoting the build-up of adenosine, a potent anti-inflammatory agent (Baggott et al., *Biochem. J.*, 236:193-200 (1986); Morabito et al., *J. Clin. Invest.*, 101:295-300 (1998); Montesinos et al., *Arthritis*, 48:240-247 (2003); Cronstein et al., *J. Clin. Invest.*, 92:2675-2682 (1993)). Furthermore, MTXPGs are inhibitors of thymidylate synthase (TS) (Allegra et al., *J. Biol. Chem.*, 260:9720-9726 (1985)). TS methylates deoxyuridine monophosphate to produce deoxythymidylate, providing a unique de novo source of thymidylate.

Part of the large inter-individual variability in the response to methotrexate is related to common polymorphisms in genes implicated in methotrexate pharmacokinetics or pharmacodynamics (Relling and Dervieux, *Nat. Rev. Cancer*, 1:99-108 (2001)). Recently, a G to A transition in exon 1 (position 80) of RFC-1, resulting in an arginine to histidine substitution at codon 27, was identified (Chango et al., *Mol. Genet. Metab.*, 70:310-315 (2000)). However, the functional consequence of this polymorphism on methotrexate transport has remained unclear (Whetstine et al., *Clin. Cancer Res.*, 7:3416-3422 (2001); Laverdiere et al., *Blood*, 100:3832-3834 (2002)). Moreover, a recent study of children with acute lymphoblastic leukemia has suggested that the A variant may be associated with poor clinical outcomes as compared with patients having the G/G genotype; individuals carrying the A/A genotype presented higher plasma concentrations of methotrexate compared to those with the G/G or G/A genotypes (Laverdiere et al., supra, (2002)).

Because individual differences in pharmacokinetic and pharmacodynamic parameters can be difficult to predict and because patient genotype affects these parameters, methotrexate treatment can be rendered safer and more effective through patient genotyping. Thus, there exists a need for novel correlations between patient genotypes and efficacy of methotrexate therapy. There also exists a need for new methods of determining or optimizing the efficacy of methotrexate therapy by determining MTXPG levels in a patient through genotyping. The present invention satisfies these needs and provides related advantages as well.

BRIEF SUMMARY OF THE INVENTION

The present invention provides methods for determining a level of methotrexate polyglutamates (MTXPGs) in an individual undergoing methotrexate (MTX) therapy and for optimizing dose efficacy of MTX therapy in an individual by genotyping the individual at a polymorphic site in at least one folate pathway gene (e.g., a reduced folate carrier (RFC-1) gene, a gamma glutamyl hydrolase (GGH) gene, etc.). Methods are also provided for determining a level of MTXPGs in an individual undergoing MTX therapy and for optimizing dose efficacy of MTX therapy in an individual by generating a pharmacogenetic index based upon the genotype of the individual at a polymorphic site in an RFC-1 gene and/or a GGH gene.

As such, in one aspect, the present invention provides methods for determining a level of methotrexate polyglutamates (MTXPGs) in an individual undergoing methotrexate therapy, the method comprising:

genotyping the individual at a polymorphic site in at least one folate pathway gene, wherein the presence of a variant allele at the polymorphic site is indicative of the level of MTXPGs in the individual.

In another aspect, the present invention provides methods for determining a level of MTXPGs in an individual undergoing methotrexate therapy, the method comprising:

genotyping the individual at a polymorphic site in at least one gene selected from the group consisting of a reduced folate carrier (RFC-1) gene, a gamma glutamyl hydrolase (GGH) gene, and a combination thereof, wherein the presence of a variant allele at the polymorphic site is indicative of the level of MTXPGs in the individual.

In yet another aspect, the present invention provides methods for determining a level of MTXPGs in an individual undergoing methotrexate therapy, the method comprising:

determining whether the individual is homozygous for a 80 G to A mutation in the RFC-1 coding region, wherein the presence of the homozygous 80 G to A mutation is indicative of an increased level of MTXPGs relative to wild-type or heterozygous individuals.

In still yet another aspect, the present invention provides methods for determining a level of MTXPGs in an individual undergoing methotrexate therapy, the method comprising:

determining whether the individual is homozygous for a −401 C to T mutation in the GGH promoter, wherein the presence of the homozygous −401 C to T mutation is indicative of a decreased level of MTXPGs relative to wild-type or heterozygous individuals.

In a further aspect, the present invention provides assay methods for optimizing dose efficacy of methotrexate therapy in an individual, the method comprising:

a) genotyping the individual at a polymorphic site in at least one folate pathway gene to determine a level of MTXPGs in the individual; and b) recommending a subsequent dose of methotrexate or an analog thereof based upon the level of MTXPGs in the individual.

In another aspect, the present invention provides methods for determining a level of MTXPGs in an individual undergoing methotrexate therapy, the method comprising:

a) determining whether the individual has a variant allele in at least one gene selected from the group consisting of an RFC-1 gene, a GGH gene, and a combination thereof; and b) generating a pharmacogenetic index based upon the presence or absence of the variant allele, wherein the pharmacogenetic index is indicative of the level of MTXPGs in the individual.

In yet another aspect, the present invention provides methods for determining a level of MTXPGs in an individual undergoing methotrexate therapy, the method comprising:

a) genotyping the individual at a polymorphic site in an RFC-1 gene and a GGH gene;

b) identifying the presence or absence of a variant allele at the polymorphic site in the RFC-1 and GGH genes;

c) determining whether the individual is wild-type, heterozygous, or homozygous for the variant alleles in the RFC-1 and GGH genes;

d) assigning to the RFC-1 or GGH gene a value of 0 when the individual is wild-type or heterozygous for the variant allele or a value of 1 when the individual is homozygous for the variant allele; and e) generating a pharmacogenetic index by subtracting the value assigned to the GGH gene from the value assigned to the RFC-1 gene, wherein the pharmacogenetic index is indicative of the level of MTXPGs in the individual.

In still yet another aspect, the present invention provides assay methods for optimizing dose efficacy of methotrexate therapy in an individual, the method comprising:

a) determining whether the individual has a variant allele in at least one gene selected from the group consisting of an RFC-1 gene, a GGH gene, and a combination thereof;

b) generating a pharmacogenetic index based upon the presence or absence of the variant allele; and c) recommending a subsequent dose of methotrexate or an analog thereof based upon the pharmacogenetic index.

In a further aspect, the present invention provides systems for determining a level of MTXPGs in an individual undergoing methotrexate therapy, the system comprising:

a) a genotypic profile module for genotyping the individual at a polymorphic site in at least one gene selected from the group consisting of an RFC-1 gene, a GGH gene, and a combination thereof; and b) a pharmacogenetic profile module for generating a pharmacogenetic index to determine the level of MTXPGs in the individual.

In an additional aspect, the present invention provides kits for determining a level of MTXPGs in an individual undergoing methotrexate therapy, the kit comprising:

a) a genotypic profile module for genotyping the individual at a polymorphic site in at least one gene selected from the group consisting of an RFC-1 gene, a GGH gene, and a combination thereof; and b) a pharmacogenetic profile module for generating a pharmacogenetic index to determine the level of MTXPGs in the individual.

Other objects, features, and advantages of the present invention will be apparent to one of skill in the art from the following detailed description and figures.

BRIEF DESCRIPTION OF THE DRAWINGS

FIG. 1A: the chemical structure of methotrexate. FIG. 1B: the chemical structure of methotrexate polyglutamates, wherein N refers to the number of glutamates attached to methotrexate.

FIG. 2A: scatterplot of predicted versus observed $MTXPG_{1-5}$ concentrations. FIG. 2B: scatterplot of predicted versus observed $MTXPG_{3-5}$ concentrations.

FIG. 3A: Increased PI, e.g., from −1 to 1, was associated with increased $MTXPG_{1-5}$ levels (p=0.057) and increased $MTXPG_{3-5}$ levels (p=0.027). FIG. 3B: Increased PI, e.g., from −1 to 1, was associated with increased MTXPG$_5$ levels (p=0.0006), MTXPG$_4$ levels (p=0.035), and MTXPG$_3$ levels (p=0.027).

DETAILED DESCRIPTION OF THE INVENTION

I. Definitions

As used herein, the following terms have the meanings ascribed to them unless specified otherwise.

Figure 1:
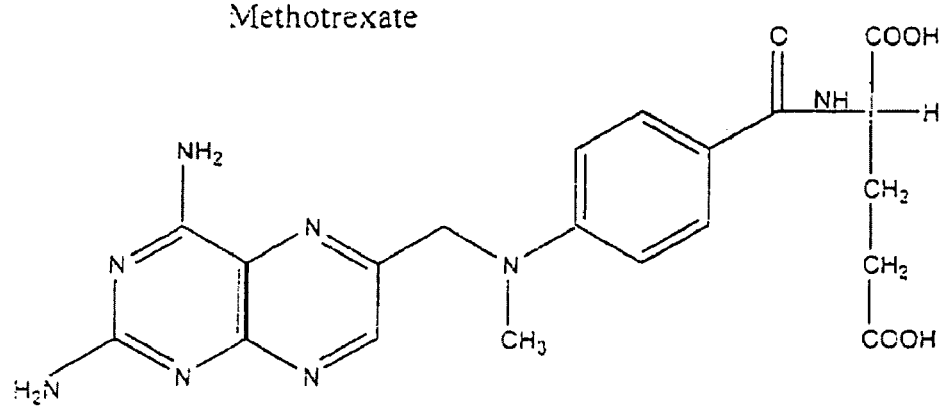
FIG. 1 shows the structures of methotrexate and methotrexate polyglutamates.
Figure 1:
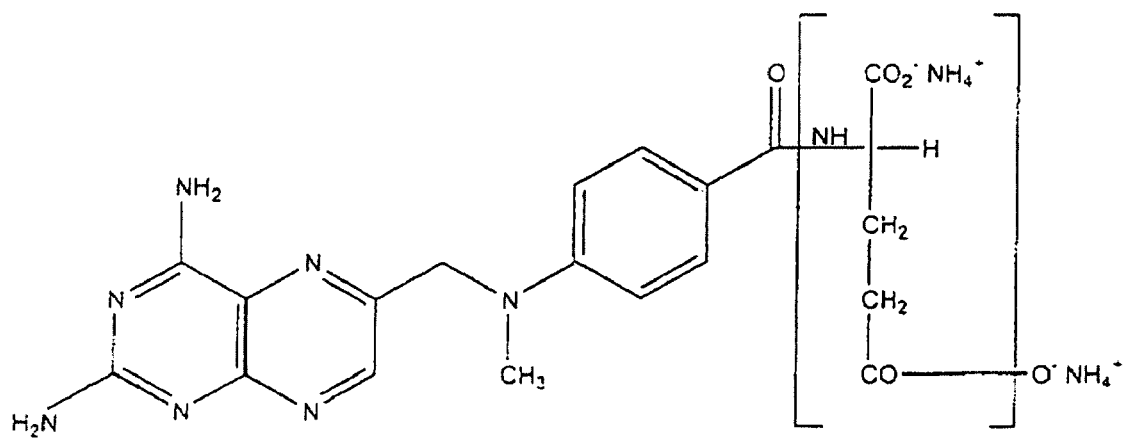

The term "methotrexate" is synonymous with "MTX" and refers to a molecule having the structure shown in FIG. 1A. Methotrexate includes, in part, a 2,4-diamino substituted pterine ring moiety linked at the 6 position to the amino group of a p-aminobenzoyl moiety, the p-aminobenzoyl moiety having a methylated amino group and being amide bonded to a glutamic acid moiety. As used herein, "MTXPG$_1$" is synonymous with methotrexate.

The term "methotrexate polyglutamate" is synonymous with "MTXPG" and refers to a derivative of methotrexate having two or more glutamates which are amide bonded to the p-aminobenzoyl moiety of methotrexate as shown in the generalized structure of FIG. 1B. The number of glutamates in a methotrexate polyglutamate varies from two to seven or more; the number of glutamate moieties can be denoted by "n" using the nomenclature MTXPG$_n$ such that, for example, MTXPG$_2$ is MTXPG having two glutamates, MTXPG$_3$ is MTXPG having three glutamates, MTXPG$_4$ is MTXPG having four glutamates, MTXPG$_5$ is MTXPG having five glutamates, MTXPG$_6$ is MTXPG having six glutamates, MTXPG$_7$ is MTXPG having seven glutamates, and MTXPG$_{3-5}$ is a mixture containing MTXPG$_3$, MTXPG$_4$, and MTXPG$_5$, with the ratio of the individual polyglutamated forms in the mixture not defined.

The term "methotrexate therapy" or "MTX therapy" refers to the treatment of any of a variety of inflammatory diseases, autoimmune diseases, and cancers using methotrexate or an analog thereof. A "methotrexate analog" is a compound having structural and functional similarity to methotrexate and includes, without limitation, 4-amino derivatives with halogen substitution on the para-aminobenzoic moiety such as dichloromethotrexate, 7-methyl substituted MTX, 3',5'-difluoro MTX, 2' and 3' monofluorinated derivatives of aminopterin, and 7,8-dihydro-8-methyl-MTX. One skilled in the art will appreciate that the term methotrexate therapy includes other anti-folate compounds such as aminopterin, raltitrexed, lometrexol, multitargeted anti-folate (MTA), AQA, edetrexate, lomotrexol, BW1843U89, ZD1694, and analogs thereof. One skilled in the art will also appreciate that methotrexate can be used in a combination therapy with one or more methotrexate analogs and/or other anti-folate compounds.

The term "inflammatory disease" refers to a disease or disorder characterized or caused by inflammation. "Inflammation" refers to a local response to cellular injury that is marked by capillary dilatation, leukocytic infiltration, redness, heat, and pain that serves as a mechanism initiating the elimination of noxious agents and of damaged tissue. The site of inflammation includes the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Such inflammatory diseases include, but are not limited to, inflammatory bowel disease, rheumatoid diseases (e.g., rheumatoid arthritis), other arthritic diseases (e.g., acute arthritis, acute gouty arthritis, bacterial arthritis, chronic inflammatory arthritis, degenerative arthritis (osteoarthritis), infectious arthritis, juvenile arthritis, mycotic arthritis, neuropathic arthritis, polyarthritis, proliferative arthritis, psoriatic arthritis, venereal arthritis, viral arthritis), fibrositis, pelvic inflammatory disease, acne, psoriasis, actinomycosis, dysentery, biliary cirrhosis, Lyme disease, heat rash, Stevens-Johnson syndrome, mumps, pemphigus vulgaris, and blastomycosis. Inflammatory bowel diseases are chronic inflammatory diseases of the gastrointestinal tract which include, without limitation, Crohn's disease, ulcerative colitis, and indeterminate colitis. Rheumatoid arthritis is a chronic inflammatory disease primarily of the joints, usually polyarticular, marked by inflammatory changes in the synovial membranes and articular structures and by muscle atrophy and rarefaction of the bones.

The term "autoimmune disease" refers to a disease or disorder resulting from an immune response against a self tissue or tissue component and includes a self antibody response or cell-mediated response. The term autoimmune disease, as used herein, encompasses organ-specific autoimmune diseases, in which an autoimmune response is directed against a single tissue, such as Type I diabetes mellitus, myasthenia gravis, vitiligo, Graves' disease, Hashimoto's disease, Addison's disease, autoimmune gastritis, and autoimmune hepatitis. The term autoimmune disease also encompasses non-organ specific autoimmune diseases, in which an autoimmune response is directed against a component present in several or many organs throughout the body. Such autoimmune diseases include, for example, systemic lupus erythematosus, progressive systemic sclerosis and variants, polymyositis, and dermatomyositis. Additional autoimmune diseases include, but are not limited to, pernicious anemia, primary biliary cirrhosis, autoimmune thrombocytopenia, Sjogren's syndrome, and multiple sclerosis.

The term "cancer" refers to any of various malignant neoplasms characterized by the proliferation of anaplastic cells that tend to invade surrounding tissue and metastasize to new body sites. Examples of different types of cancer include, but are not limited to, lung cancer, breast cancer, bladder cancer, thyroid cancer, liver cancer, pleural cancer, pancreatic cancer, ovarian cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers, blood cancers, osteogenic sarcomas, B-cell lymphoma, non-Hodgkin's lymphoma, Burkitt's lymphoma, fibrosarcoma, neuroblastoma, glioma, melanoma, monocytic leukemia, myelogenous leukemia, acute lymphocytic leukemia, and acute myelocytic leukemia.

The term "gene" refers to the segment of DNA involved in producing a polypeptide chain; it includes regions preceding and following the coding region, such as the promoter and 3'-untranslated region, respectively, as well as intervening sequences (introns) between individual coding segments (exons).

The term "nucleic acid" or "polynucleotide" refers to deoxyribonucleotides or ribonucleotides and polymers thereof in either single- or double-stranded form including, for example, genomic DNA, cDNA, and MRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix. The term also encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), polymorphisms, alleles, orthologs, single nucleotide polymorphisms (SNPs), and complementary sequences, as well as the sequence explicitly indicated. The term nucleic acid is used interchangeably herein with gene, cDNA, and mRNA encoded by a gene.

The term "polymorphism" refers to the occurrence of two or more genetically determined alternative sequences or alleles in a population. A "polymorphic site" refers to the locus at which divergence occurs. Preferred polymorphic sites have at least two alleles, each occurring at a particular frequency in a population. A polymorphic locus may be as small as one base pair (i.e., single nucleotide polymorphism or SNP). Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele, and other alleles are designated as alternative alleles, "variant alleles," or "variances." The alleles occurring most frequently in a selected population is sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

A "single nucleotide polymorphism" or "SNP" occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term "genotype" refers to the genetic composition of an organism, including, for example, whether a diploid organism is heterozygous or homozygous for one or more variant alleles of interest.

A "folate pathway gene" refers to any gene involved in folate homeostasis and/or metabolism and includes the proteins encoded by these genes. Examples of folate pathway genes include, without limitation, reduced folate carrier (RFC-1), gamma glutamyl hydrolase (GGH), folylpolyglutamate synthase (FPGS), 5,10-methylenetetrahydrofolate reductase (MTHFR), 5-aminoimidazole-4-carboxamide ribonucleotide transformylase (ATIC), thymidylate synthase (TS), serine hydroxymethyltransferase (SHMT), dihydrofolate reductase (DHFR), 10-formyltetrahydrofolate synthetase (FTHFS), 10-fornyltetrahydrofolate dehydrogenase (FTHFD), glycinamide ribonucleotide transformylase (GART), aldehyde oxidase, influx/efflux transporters such as multidrug resistance proteins (e.g., MRP2), and combinations thereof. Preferably, the folate pathway gene is RFC-1 and/or GGH.

A "pharmacogenetic index" or "PI" is calculated to determine a level of MTXPGs in an individual undergoing MTX therapy or to optimize dose efficacy of MTX therapy in an individual. The present invention provides a variety of methods or algorithms for calculating various pharmacogenetic indexes. In one embodiment, the pharmacogenetic index is calculated as either the sum of or the difference between the number of variant alleles at one or more polymorphic sites. For example, if an individual is heterozygous for a variant allele at a polymorphic site, the variant allele contributes a value of 1 to the pharmacogenetic index. Likewise, if an individual is homozygous for a variant allele at a polymorphic site, the variant alleles contribute a value of 2 to the pharmacogenetic index. If an individual is wild-type at a polymorphic site, there is no contribution from the variant allele to the pharmacogenetic index.

In another embodiment, the pharmacogenetic index is calculated as either the sum of or the difference between the number of homozygous variant alleles at one or more polymorphic sites. For example, an individual that is homozygous for a variant allele (i.e., having 2 copies of the variant allele) contributes a value of 1 to the pharmacogenetic index. In this algorithm, if an individual is wild-type or heterozygous at a polymorphic site, there is no contribution from the variant allele to the pharmacogenetic index. In a preferred embodiment, the pharmacogenetic index is calculated as the difference between the number of homozygous variant alleles at one or more polymorphic sites in, e.g., the RFC-1 gene and the GGH gene. As such, in certain instances, a pharmacogenetic index for determining MTXPG levels in an individual can be calculated as follows: (1) the RFC-1 gene is assigned a value of 1 when an RFC-1 80A/A homozygous genotype is present or a value of 0 when an RFC-1 80G/G wild-type genotype or RFC-1 80G/A heterozygous genotype is present; (2) the GGH gene is assigned a value of 1 when a GGH −401T/T homozygous genotype is present or a value of 0 when a GGH −401C/C wild-type genotype or GGH −401C/T heterozygous genotype is present; and (3) the value assigned to the GGH gene is subtracted from the value assigned to the RFC-1 gene (i.e., RFC-1 value−GGH value).

The present invention is not limited to the foregoing methods or algorithms for generating a pharmacogenetic index. Using other statistical analyses, a pharmacogenetic index can be calculated. These methods include, for example, identifying the presence or absence of a variant allele at other polymorphic sites in other genes such as additional folate pathway genes including those described above; purine synthesis genes such as glutamine PRPP amidotransferase, glycinamide ribonucleotide (GAR) synthetase, formylglycinamide ribonucleotide (FGAR) amidotransferase, formylglycinamidine ribonucleotide (FGAM) cyclase, 5-aminoimidazole ribonucleotide (AIR) carboxylase, N-succinylo-5-aminoimidazole-4-carboxamide ribonucleotide (SAICAR) synthetase, SAICAR lyase, IMP synthase, adenylosuccinate synthetase, adenylosuccinate lyase, IMP dehydrogenase, and XMP-glutamine amidotransferase; pyrimidine synthesis genes such as ribonucleotide reductase, nucleoside diphosphate kinase, deaminase, deoxyuridine triphosphatase, aspartate transcarbamoylase, dihydroorotase, dihydroorotate dehydrogenase, orotate phosphoribosyl transferase, orotidylate decarboxylase, and cytidylate synthetase; and combinations thereof. Furthermore, certain genes or polymorphic sites can have a weighted contribution such that the importance of wild-type, homozygosity, or heterozygosity at that specific site contributes more weight to the pharmacogenetic index. Other parameters such as phenotypic parameters can also be used in the algorithms. Additional algorithms suitable for use in the present invention include, without limitation, principal component analysis, neural networks, genetic algorithms, fuzzy logic, pattern recognition, and pattern-matching algorithms. Those of skill in the art will know of other algorithms suitable for use in the present invention.

The term "genotypic profile module" refers to any device or apparatus for genotyping an individual at a polymorphic site in at least one gene. Suitable genotypic profile modules for use in the systems of the present invention include, without limitation, microarrays such as oligonucleotide or polynucleotide arrays, polymerase chain reaction (PCR)-based devices, sequencing apparatuses, or electrophoretic apparatuses. Preferably, the genotypic profile module is a microarray. A description of arrays suitable for use in the systems of the present invention is provided below.

The term "pharmacogenetic profile module" refers to any device, apparatus, software code, or a combination thereof for generating a pharmacogenetic index to determine the level of MTXPGs in the individual. Suitable pharmacogenetic profile modules for use in the systems of the present invention include, without limitation, any device or apparatus capable of calculating one or more pharmacogenetic indexes using, for example, one or more of the above-described algorithms. As a non-limiting example, computers comprising software including computer readable medium having computer executable instructions for performing algorithmic calculations are within the scope of the systems of the present invention. Alternatively, the pharmacogenetic profile module is a computer software program capable of performing algorithmic calculations to generate pharmacogenetic indexes. Suitable computer readable medium include, without limitation, floppy disk, CD-ROM/DVD/DVD-ROM, hard-disk drive, flash memory, ROM/RAM, magnetic tapes, etc. The computer executable instructions may be written in a suitable computer language or a combination of several languages. Basic computational biology methods are described in, e.g., Setubal et al., Introduction to Computational Biology Methods, PWS Publishing Company, Boston (1997); Salzberg, Searles, Kasif, (Ed.), Computational Methods in Molecular Biology, Elsevier, Amsterdam (1998); Rashidi and Buehler, Bioinformatics Basics: Application in Biological Science and Medicine, CRC Press, London (2000); and Ouelette and Bzevanis, Bioinformatics: A Practical Guide for Analysis of Gene and Proteins, Wiley & Sons, Inc., $2^{nd}$ Ed. (2001). In certain instances, the pharmacogenetic profile module of the present invention can be used in conjunction with the genotypic profile module for probe design, management of data, analysis, and/or instrument operation.

The term "sample" refers to any biological specimen obtained from an individual that contains nucleic acid. Suitable samples for use in the present invention include, without limitation, whole blood, plasma, serum, red blood cells, saliva, urine, stool (i.e., feces), tears, any other bodily fluid, tissue samples (e.g., biopsy), and cellular extracts thereof (e.g., red blood cellular extract).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to an individual. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

II. General Overview

The present invention provides methods for determining a level of methotrexate polyglutamates (MTXPGs) in an individual undergoing methotrexate (MTX) therapy and for optimizing dose efficacy of MTX therapy in an individual by genotyping the individual at a polymorphic site in at least one folate pathway gene such as a reduced folate carrier (RFC-1) gene, a gamma glutamyl hydrolase (GGH) gene, or a combination thereof. Methods are also provided for determining a level of MTXPGs in an individual undergoing MTX therapy and for optimizing dose efficacy of MTX therapy in an individual by generating a pharmacogenetic index based upon the genotype of the individual at a polymorphic site in an RFC-1 gene and/or a GGH gene.

As disclosed herein, MTX therapy was monitored in patients with rheumatoid arthritis, and novel associations between genetic polymorphisms in the folate pathway (e.g., RFC-1, GGH) and MTXPG levels were identified. In particular, the results disclosed in Example 1 indicate that variant allele homozygosity in RFC-1 and/or GGH are predictive of MTXPG levels in patients. As such, genotyping a patient at a polymorphic site in RFC-1 and/or GGH can be used to determine the level of MTXPGs in the patient, which can then be used to evaluate the efficacy of MTX therapy, to allow for the advantageous individualization of MTX dosages administered to the patient.

III. Description of the Embodiments

In one aspect, the present invention provides methods for determining a level of methotrexate polyglutamates (MTX-PGs) in an individual undergoing methotrexate therapy, the method comprising:

genotyping the individual at a polymorphic site in at least one folate pathway gene, wherein the presence of a variant allele at the polymorphic site is indicative of the level of MTXPGs in the individual.

In one embodiment, the individual has an inflammatory disease, autoimmune disease, or cancer. The individual may have an inflammatory disease such as rheumatoid arthritis. Suitable folate pathway genes for genotyping according to the methods of the present invention include, without limitation, reduced folate carrier (RFC-1), gamma glutamyl hydrolase (GGH), folylpolyglutamate synthase (FPGS), 5,10-methylenetetrahydrofolate reductase (MTHFR), 5-aminoimidazole-4-carboxamide ribonucleotide transformylase (ATIC), thymidylate synthase (TS), serine hydroxymethyltransferase (SHMT), dihydrofolate reductase (DHFR), 10-formyltetrahydrofolate synthetase (FTHFS), 10-formyltetrahydrofolate dehydrogenase (FTHFD), glycinamide ribonucleotide transformylase (GART), aldehyde oxidase, influx/efflux transporters such as multidrug resistance proteins (e.g., MRP2), and combinations thereof. Preferably, the folate pathway gene is RFC-1, GGH, or a combination thereof.

In another embodiment, the individual is wild-type, heterozygous, or homozygous for the variant allele at the polymorphic site. Preferably, the individual is homozygous for the variant allele. In certain instances, the individual homozygous for the variant allele has an increased level of MTXPGs relative to wild-type or heterozygous individuals. In certain other instances, the individual homozygous for the variant allele has a decreased level of MTXPGs relative to wild-type or heterozygous individuals.

In some embodiments, the methods of the present invention further comprise recommending (e.g., to a clinician) a subsequent dose of methotrexate or an analog thereof based upon the level of MTXPGs in the individual. As used herein, the term "recommend" or "recommending" refers to providing dosing instructions for a drug (e.g., methotrexate or an analog thereof) based on the level of MTXPGs in the individual. Dosing instructions include, for example, lab results with preferred drug doses, data sheets, look-up tables setting forth preferred drug doses, instructions or guidelines for using the drugs, package inserts to accompany the drug, and the like. As a non-limiting example, in instances where the presence of a variant allele is indicative of an increased level of MTXPGs in the individual, the methods of the present invention may further comprise recommending that the subsequent dose of methotrexate or an analog thereof be maintained or decreased (e.g., to low-dose MTX therapy) to reduce or prevent side-effects. Alternatively, in instances where the presence of a variant allele is indicative of a decreased level of MTXPGs in the individual, the methods of the present invention may further comprise recommending that the subsequent dose of methotrexate or an analog thereof be increased (e.g., to high-dose MTX therapy).

In another aspect, the present invention provides methods for determining a level of methotrexate polyglutamates (MTXPGs) in an individual undergoing methotrexate therapy, the method comprising:

genotyping the individual at a polymorphic site in at least one gene selected from the group consisting of a reduced folate carrier (RFC-1) gene, a gamma glutamyl hydrolase (GGH) gene, and a combination thereof, wherein the presence of a variant allele at the polymorphic site is indicative of the level of MTXPGs in the individual.

In one embodiment, the individual has an inflammatory disease, autoimmune disease, or cancer. Preferably, the individual has rheumatoid arthritis. In another embodiment, the individual is wild-type, heterozygous, or homozygous for the variant allele at the polymorphic site. In a preferred embodiment, the individual is homozygous for the variant allele in the RFC-1 gene. In certain instances, the individual homozygous for the variant allele has increased RFC-1 activity. Alternatively, the individual has decreased RFC-1 activity. In certain other instances, the individual homozygous for the variant allele has an increased level of MTXPGs relative to wild-type or heterozygous individuals. Alternatively, the individual has a decreased level of MTXPGs relative to wild-type or heterozygous individuals.

In another preferred embodiment, the individual is homozygous for the variant allele in the GGH gene. In certain instances, the individual homozygous for the variant allele has increased GGH activity. Alternatively, the individual has decreased GGH activity. In certain other instances, the individual homozygous for the variant allele has an increased level of MTXPGs relative to wild-type or heterozygous individuals. Alternatively, the individual has a decreased level of MTXPGs relative to wild-type or heterozygous individuals.

In yet another embodiment, the individual is homozygous for the variant allele in the RFC-1 gene and the GGH gene. In certain instances, the individual homozygous for both variant alleles has an increased level of MTXPGs relative to wild-type or heterozygous individuals. Alternatively, the individual has a decreased level of MTXPGs relative to wild-type or heterozygous individuals. In certain other instances, the individual homozygous for both variant alleles has a similar level of MTXPGs relative to wild-type or heterozygous individuals.

In still yet another embodiment, the variant allele in the RFC-1 gene comprises a 80 G to A mutation in the RFC-1 coding region. Preferably, the individual is homozygous for the RFC-1 80A mutation. In certain instances, the individual homozygous for the RFC-1 80A mutation has an increased level of MTXPGs relative to wild-type or heterozygous individuals. In a further embodiment, the variant allele in the GGH gene comprises a −401 C to T mutation in the GGH promoter. In a preferred embodiment, the individual is homozygous for the GGH −401T mutation. In certain instances, the individual homozygous for the GGH −401T mutation has a decreased level of MTXPGs relative to wild-type or heterozygous individuals.

In some embodiments, the level of MTXPGs comprises $MTXPG_{1-5}$. In other embodiments, the level of MTXPGs comprises $MTXPG_{3-5}$. In certain instances, the level of MTXPGs is determined using a multivariate linear regression analysis. Preferably, the level of $MTXPG_{1-5}$ is determined according to the formula:

$$MTXPG_{1-5}(nmol/L) = intercept + (\beta_1 \times Age) + (\beta_2 \times Dose) + (\beta_3 \times \text{Route of Administration}) + (\beta_4 \times \text{RFC-1 genotype}) + (\beta_5 \times \text{GGH genotype}),$$

wherein
intercept=−103±16,
$\beta_1$=2.47±0.29,
$\beta_2$=4.95±0.78,
$\beta_3$=16.2±8.0,
$\beta_4$=20.8±9.7,
$\beta_5$=−21.0±9.6,
Route of Administration=0 for oral or 1 for injected,
RFC-1 genotype=0 for 80G/G or 80G/A or 1 for 80A/A, and
GGH genotype=0 for −401C/C or −401C/T or 1 for −401T/T.

In another preferred embodiment, the level of $MTXPG_{3-5}$ is determined according to the formula:

$$MTXPG_{3-5}(nmol/L) = intercept + (\beta_1 \times Age) + (\beta_2 \times Dose) + (\beta_3 \times \text{Route of Administration}) + (\beta_4 \times \text{RFC-1 genotype}) + (\beta_5 \times \text{GGH genotype}),$$

wherein
intercept=−120±24,
$\beta_1$=1.53±0.20,
$\beta_2$=4.39±0.53,
$\beta_3$=15.6±5.4,
$\beta_4$=14.8±6.6,
$\beta_5$=−15.3±6.5,
Route of Administration=0 for oral or 1 for injected,
RFC-1 genotype=0 for 80G/G or 80G/A or 1 for 80A/A, and
GGH genotype=0 for −401C/C or −401C/T or 1 for −401T/T.

In additional embodiments of the present invention, the methods further comprise genotyping the individual at a polymorphic site in other folate pathway genes, purine synthesis genes, pyrimidine synthesis genes, and combinations thereof. In certain instances, the genotyping is performed on a nucleic acid sample obtained from whole blood. However, one skilled in the art will appreciate that any other sample containing nucleic acid is suitable for use in the methods of the present invention.

In yet another aspect, the present invention provides methods for determining a level of MTXPGs in an individual undergoing methotrexate therapy, the method comprising:

determining whether the individual is homozygous for a 80 G to A mutation in the RFC-1 coding region, wherein the presence of the homozygous 80 G to A mutation is indicative of an increased level of MTXPGs relative to wild-type or heterozygous individuals.

In still yet another aspect, the present invention provides methods for determining a level of MTXPGs in an individual undergoing methotrexate therapy, the method comprising:

determining whether the individual is homozygous for a −401 C to T mutation in the GGH promoter, wherein the presence of the homozygous −401 C to T mutation is indicative of a decreased level of MTXPGs relative to wild-type or heterozygous individuals.

In a further aspect, the present invention provides assay methods for optimizing dose efficacy of methotrexate therapy in an individual, the method comprising:

a) genotyping the individual at a polymorphic site in at least one folate pathway gene to determine a level of MTXPGs in the individual; and b) recommending a subsequent dose of methotrexate or an analog thereof based upon the level of MTXPGs in the individual.

In one embodiment, the individual has an inflammatory disease, autoimmune disease, or cancer. The individual may have an inflammatory disease such as rheumatoid arthritis. Suitable folate pathway genes for genotyping according to the methods of the present invention include, without limitation, reduced folate carrier (RFC-1), gamma glutamyl hydrolase (GGH), folylpolyglutamate synthase (FPGS), 5,10-methylenetetrahydrofolate reductase (MTHFR), 5-aminoimidazole-4-carboxamide ribonucleotide transformylase (ATIC), thymidylate synthase (TS), serine hydroxymethyltransferase (SHMI), dihydrofolate reductase (DHFR), 10-formyltetrahydrofolate synthetase (FTHFS), 10-formyltetrahydrofolate dehydrogenase (FTHFD), glycinamide ribonucleotide transformylase (GART), aldehyde oxidase, influx/efflux transporters such as multidrug resistance proteins (e.g., MRP2), and combinations thereof. Preferably, the folate pathway gene is RFC-1, GGH, or a combination thereof.

In another embodiment, the individual is wild-type, heterozygous, or homozygous for the variant allele at the polymorphic site. Preferably, the individual is homozygous for the variant allele. In certain instances, the individual homozygous for the variant allele has an increased level of MTXPGs relative to wild-type or heterozygous individuals. In certain other instances, the individual homozygous for the variant allele has a decreased level of MTXPGs relative to wild-type or heterozygous individuals.

In a preferred embodiment, the individual is homozygous for the variant allele in the RFC-1 gene. In certain instances, the individual homozygous for the variant allele has increased RFC-1 activity. Alternatively, the individual has decreased RFC-1 activity. In certain other instances, the individual homozygous for the variant allele has an increased level of MTXPGs relative to wild-type or heterozygous individuals. Alternatively, the individual has a decreased level of MTXPGs relative to wild-type or heterozygous individuals.

In another preferred embodiment, the individual is homozygous for the variant allele in the GGH gene. In certain instances, the individual homozygous for the variant allele has increased GGH activity. Alternatively, the individual has decreased GGH activity. In certain other instances, the individual homozygous for the variant allele has an increased level of MTXPGs relative to wild-type or heterozygous individuals. Alternatively, the individual has a decreased level of MTXPGs relative to wild-type or heterozygous individuals.

In yet another embodiment, the variant allele in the RFC-1 gene comprises a 80 G to A mutation in the RFC-1 coding region. Preferably, the individual is homozygous for the RFC-1 80A mutation. In certain instances, the individual homozygous for the RFC-1 80A mutation has an increased level of MTXPGs relative to wild-type or heterozygous individuals. In a further embodiment, the variant allele in the GGH gene comprises a −401 C to T mutation in the GGH promoter. In a preferred embodiment, the individual is homozygous for the GGH −401T mutation. In certain instances, the individual homozygous for the GGH −401T mutation has a decreased level of MTXPGs relative to wild-type or heterozygous individuals.

The assay methods of the present invention comprise recommending (e.g., to a clinician) a subsequent dose of methotrexate or an analog thereof based upon the level of MTXPGs in the individual. As described above, the term "recommend" or "recommending" refers to providing dosing instructions for a drug such as methotrexate or an analog thereof based on the level of MTXPGs in the individual. As a non-limiting example, in instances where the presence of a variant allele is indicative of an increased level of MTXPGs in the individual (e.g., relative to wild-type or heterozygous individuals), the assay methods of the present invention comprise recommending that the subsequent dose of methotrexate or an analog thereof be maintained or decreased (e.g., to low-dose MTX therapy) to reduce or prevent side-effects. Alternatively, in instances where the presence of a variant allele is indicative of a decreased level of MTXPGs in the individual (e.g., relative to wild-type or heterozygous individuals), the assay methods of the present invention comprise recommending that the subsequent dose of methotrexate or an analog thereof be increased (e.g., to high-dose MTX therapy).

In another aspect, the present invention provides methods for determining a level of MTXPGs in an individual undergoing methotrexate therapy, the method comprising:

a) determining whether the individual has a variant allele in at least one gene selected from the group consisting of an RFC-1 gene, a GGH gene, and a combination thereof; and b) generating a pharmacogenetic index based upon the presence or absence of the variant allele, wherein the pharmacogenetic index is indicative of the level of MTXPGs in the individual.

The present invention provides a variety of methods or algorithms for generating various pharmacogenetic indexes. In one embodiment, the pharmacogenetic index is calculated as either the sum of or the difference between the number of variant alleles at one or more polymorphic sites in RFC-1, GGH, or a combination thereof. In another embodiment, the pharmacogenetic index is calculated as either the sum of or the difference between the number of homozygous variant alleles at one or more polymorphic sites in RFC-1, GGH, or a combination thereof. In a preferred embodiment, the pharmacogenetic index is calculated as the difference between the number of homozygous variant alleles at one or more polymorphic sites in RFC-1 and GGH.

As such, in certain instances, the present invention provides methods for determining a level of MTXPGs in an individual undergoing methotrexate therapy, the method comprising:

a) genotyping the individual at a polymorphic site in an RFC-1 gene and a GGH gene;

b) identifying the presence or absence of a variant allele at the polymorphic site in the RFC-1 and GGH genes;

c) determining whether the individual is wild-type, heterozygous, or homozygous for the variant alleles in the RFC-1 and GGH genes;

d) assigning to the RFC-1 or GGH gene a value of 0 when the individual is wild-type or heterozygous for the variant allele or a value of 1 when the individual is homozygous for the variant allele; and e) generating a pharmacogenetic index by subtracting the value assigned to the GGH gene from the value assigned to the RFC-1 gene, wherein the pharmacogenetic index is indicative of the level of MTXPGs in the individual.

In one embodiment, the level of MTXPGs comprises MTXPG$_{3-5}$. In certain instances, the pharmacogenetic index is indicative of an increase in the level of MTXPGs relative to wild-type individuals. In these instances, the pharmacogenetic index has a value of 1. In certain other instances, the pharmacogenetic index is indicative of a decrease in the level of MTXPGs relative to wild-type individuals. In these instances, the pharmacogenetic index has a value of −1.

In another embodiment, the pharmacogenetic index is indicative of a probability that the level of MTXPGs is above a median level. As a non-limiting example, the median level is about 56 nmol/L. Other median levels suitable for the methods of the present invention include, without limitation, about 20, 25, 30, 35, 40, 45, 50, 51, 52, 53, 54, 55, 57, 58, 59, 60, 65, 70, 75, 80, 85, 90, 95, and 100 nmol/L. In certain instances, the pharmacogenetic index is indicative of an increase in the probability that the level of MTXPGs is above said median level relative to wild-type individuals. In these instances, the pharmacogenetic index has a value of 1. In certain other instances, the pharmacogenetic index is indicative of a decrease in the probability that the level of MTXPGs is above said median level relative to wild-type individuals. In these instances, the pharmacogenetic index has a value of −1.

In yet another aspect, the present invention provides assay methods for optimizing dose efficacy of methotrexate therapy in an individual, the method comprising:

a) determining whether the individual has a variant allele in at least one gene selected from the group consisting of an RFC-1 gene, a GGH gene, and a combination thereof;

b) generating a pharmacogenetic index based upon the presence or absence of the variant allele; and c) recommending a subsequent dose of methotrexate or an analog thereof based upon the pharmacogenetic index.

In certain instances, the pharmacogenetic index is indicative of an increase in the level of MTXPGs relative to wild-type individuals. In these instances, the assay methods of the present invention comprise recommending that the subsequent dose of methotrexate or an analog thereof be maintained or decreased (e.g., to low-dose MTX therapy) to reduce or prevent side-effects. Alternatively, in instances where the pharmacogenetic index is indicative of a decreased level of MTXPGs relative to wild-type individuals, the assay methods of the present invention comprise recommending that the subsequent dose of methotrexate or an analog thereof be increased (e.g., to high-dose MTX therapy).

In a further aspect, the present invention provides systems for determining a level of MTXPGs in an individual undergoing methotrexate therapy, the system comprising:

a) a genotypic profile module for genotyping the individual at a polymorphic site in at least one gene selected from the group consisting of an RFC-1 gene, a GGH gene, and a combination thereof; and b) a pharmacogenetic profile module for generating a pharmacogenetic index to determine the level of MTXPGs in the individual.

In one embodiment, the individual has an inflammatory disease, autoimmune disease, or cancer. The individual may have an inflammatory disease such as rheumatoid arthritis. In another embodiment, the genotypic profile module is any device or apparatus suitable for genotyping the individual at a polymorphic site in RFC-1, GGH, or a combination thereof. Examples of genotypic profile modules include, without limitation, microarrays such as oligonucleotide or polynucleotide arrays, polymerase chain reaction (PCR)-based devices, sequencing apparatuses, and electrophoretic apparatuses. In certain instances, the microarray comprises a plurality of nucleic acid probes which hybridize to RFC-1 or GGH. In yet another embodiment, the pharmacogenetic profile module is any device or apparatus suitable for generating a pharmacogenetic index to determine the level of MTXPGs in the individual. Examples of pharmacogenetic profile modules include, without limitation, computer software programs capable of performing algorithmic calculations to generate pharmacogenetic indexes and computers containing such software programs. In certain instances, the algorithm is based upon the presence or absence of a variant allele in RFC-1, GGH, or a combination thereof. One skilled in the art will know of additional genotypic profile modules and pharmacogenetic profile modules suitable for use in the systems of the present invention.

In an additional aspect, the present invention provides kits for determining a level of MTXPGs in an individual undergoing methotrexate therapy, the kit comprising:

a) a genotypic profile module for genotyping the individual at a polymorphic site in at least one gene selected from the group consisting of an RFC-1 gene, a GGH gene, and a combination thereof; and b) a pharmacogenetic profile module for generating a pharmacogenetic index to determine the level of MTXPGs in the individual.

In one embodiment, the kit further comprises directions for use of the genotypic profile module and the pharmacogenetic profile module. Suitable genotypic profile modules and pharmacogenetic profile modules for use in the kits of the present invention are described above. Preferably, the genotypic profile module is a microarray such as an oligonucleotide or polynucleotide array.

A. Methotrexate Therapy

Methotrexate is well known in the art as an inhibitor of dihydrofolate reductase (DHFR), which acts to decrease production of tetrahydrofolate (THF) from dihydrofolate (DHF). As a consequence, methotrexate indirectly inhibits purine and thymidine synthesis and amino acid interconversion. Methotrexate also exhibits anti-proliferative activity through inhibition of thymidylate synthesis, which is required to synthesize DNA (Calvert, *Semin. Oncol.*, 26:3-10 (1999)). Methotrexate, its synthesis, and its properties are described in further detail in U.S. Pat. Nos. 2,512,572; 3,892,801; 3,989,703; 4,057,548; 4,067,867; 4,079,056; 4,080,325; 4,136,101; 4,224,446; 4,306,064; 4,374,987; 4,421,913; and 4,767,859. Methods for using methotrexate to treat cancer are described, for example, in U.S. Pat. Nos. 4,106,488; 4,558,690; and 4,662,359.

Methotrexate, which is useful in the treatment of a variety of inflammatory diseases, autoimmune diseases, and cancers, can be administered by oral or parenteral routes. The drug is readily distributed to body tissues, where it is transported into cells by a specific carrier system that includes components such as the reduced folate carrier (RFC-1) and the folate receptor. Due to its high polarity at physiological pH, methotrexate does not readily pass through the cell membrane, and the majority of the drug enters cells via specific carriers. Once inside the cell, methotrexate is converted to methotrexate polyglutamates (MTXPGs) by specific enzymes such as folylpolyglutamate synthase (FPGS), which adds one or more glutamic acid moieties, linked by iso-peptidic bonds to the γ-carboxyl of methotrexate as described, e.g., in Kamen, Semin. Oncol., S18:30-39 (1997).

The methods of the present invention also can be used to determine a level of a polyglutamated methotrexate analog or other polyglutamylatable anti-folate compounds. As used herein, the term "methotrexate analog" refers to a compound having structural and functional similarity to methotrexate. Methotrexate analogs are functionally characterized, in part, by their inhibitory activity against dihydrofolate reductase (DHFR). A methotrexate analog useful in the present invention acts as a substrate for polyglutamation in a cell by an enzyme such as FPGS. Methotrexate analogs include, without limitation, 4-amino derivatives with halogen substitution on the para-aminobenzoic moiety, such as dichloromethotrexate (see, for example, Frei et al., Clin. Pharmacol. Therap., 6:160-71 (1965)); 7-methyl substituted MTX (see, for example, Rosowsky et al., J. Med. Chem., 17:1308-11 (1974)); 3',5'-difluoro MTX, (see, for example, Tomcuf, J. Organic Chem., 26:3351 (1961)); 2' and 3' monofluorinated derivatives of aminopterin (see, for example, Henkin et al., J. Med. Chem., 26:1193-1196 (1983)); and 7,8-dihydro-8-methyl-MTX (see, for example, Chaykovsky, J. Org. Chem., 40:145-146 (1975)).

As used herein, the term "anti-folate" refers to a compound having structural similarity to folate and activity as a folate antagonist against one or more folate-dependent enzymes. Polyglutamylatable anti-folate compounds are anti-folate compounds that can be polyglutamated in a cell by an enzyme such as FPGS. Examples of polyglutamylatable anti-folate compounds include, without limitation, methotrexate (MTX), aminopterin, raltitrexed, lometrexol, multitargeted anti-folate (MTA), AQA, and analogs thereof. Aminopterin, for example, possesses a hydrogen instead of a methyl group at position N-10 compared to the structure of methotrexate. Raltitrexed is a selective inhibitor of thymidylate synthase as described, e.g., in Kamen, supra. Lometrexol selectively inhibits glycinamide ribonucleotide formyltransferase, the first enzyme involved in the pathway of de novo purine synthesis as described, for example, in Calvert, supra. Multitargeted anti-folate (MTA) is an inhibitor of multiple folate-dependent enzymes, such as dihydrofolate reductase, thymidylate synthase, and glycinamide ribonucleotide formyltransferase (see, e.g., Calvert, supra). Other anti-folate compounds suitable for use in the presence invention include, for example, edetrexate, lomotrexol, BW1843U89, and ZD1694. In certain instances, methotrexate is used in a combination therapy with one or more methotrexate analogs and/or other polyglutamylatable anti-folate compounds. The skilled person in the art understands that the methods of the present invention can be used to determine a level of a polyglutamated methotrexate analog or other polyglutamylatable anti-folate compounds in the same manner as disclosed herein for methotrexate polyglutamates.

Rheumatoid arthritis and a variety of other inflammatory diseases or autoimmune disorders such as psoriasis, systemic lupus erythematosus, and graft-versus-host disease are typically treated with low-dose methotrexate therapy, which is also used in some cancer treatment regimens. In one embodiment, the present invention provides methods for determining a level of MTXPGs in an individual or for optimizing dose efficacy of MTX therapy in an individual undergoing low-dose MTX therapy. As used herein, the term "low-dose MTX therapy" refers to administration of methotrexate to an individual at a dose that is less than 40 mg/M$^2$ of body surface per week. Typically, low-dose methotrexate therapy is administered orally at a dose in the range of 2.5 to 40 mg/M$^2$ of body surface per week, for example, 2.5 to 25 mg/m$^2$ of body surface per week depending upon the condition being treated. In certain instances, when low-dose MTX therapy provides therapeutically effective levels of MTXPGs in an individual, the dose of MTX administered to the individual is not changed. In certain other instances, when low-dose MTX therapy provides therapeutically ineffective levels of MTX-PGs in an individual, a higher dose of MTX (e.g., greater than 40 mg/m$^2$ of body surface per week) is administered to the individual.

In another embodiment, the present invention provides methods for determining a level of MTXPGs in an individual or for optimizing dose efficacy of MTX therapy in an individual undergoing high-dose MTX therapy. As used herein, the term "high-dose MTX therapy" refers to administration of methotrexate to an individual at a dose that is at least 40 mg/m$^2$ of body surface per day, for example, at least 100, 500, 1000, 1500, 3000, or 5000 mg/m$^2$ of body surface per day. One skilled in the art understands that high-dose methotrexate therapy is frequently used as an anti-cancer therapeutic and can be administered at doses up to 5 g/m$^2$ of body surface per day or higher depending upon the condition or disease being treated. One skilled in the art recognizes that the doses of methotrexate typically used in high-dose MTX therapy can be administered, for example, intravenously or orally and that such high-dose methotrexate therapy generally requires a period of recovery, which can include leucovorin rescue or another form of folate replacement. In certain instances, when high-dose MTX therapy provides therapeutically effective levels of MTXPGs in an individual, the dose of MTX administered to the individual is not changed, but the dose can also be decreased to obtain a more optimal balance of high therapeutic efficacy and low adverse effects. In certain other instances, when high-dose MTX therapy provides therapeutically ineffective levels of MTXPGs in an individual, a higher dose of MTX is administered to the individual.

It will be understood that the dosage ranges of methotrexate set forth above in the definitions of low-dose and high-dose MTX therapy are generalized with respect to treatment of a variety of diseases and that the range of methotrexate dose that is administered for one disease can differ from the range administered for another. Accordingly, a dose of 40 mg/m$^2$ of body surface per day, although generally considered high-dose methotrexate therapy, may be considered by those skilled in the art of cancer therapy as a relatively low dose for treating cancer. Similarly, a dose of 30 mg/m$^2$ of body surface per day, although generally considered as low-dose methotrexate therapy, may be considered by those skilled in the art of rheumatology as a relatively high-dose for treating rheumatoid arthritis.

B. Diseases and Disorders

The methods of the present invention can be useful for determining a level of MTXPGs in an individual or for optimizing the efficacy of methotrexate or an analog thereof in an individual on MTX therapy, including low-dose and high-dose methotrexate therapy. In one embodiment, the present invention provides methods for determining a level of MTX-PGs in an individual on MTX therapy or for optimizing dose efficacy of MTX therapy in an individual having an inflammatory disease or an autoimmune disease. In certain instances, methotrexate is used for the treatment of an inflammatory disease such as inflammatory bowel disease, rheumatoid disease (e.g., rheumatoid arthritis), other arthritic diseases, fibrositis, pelvic inflammatory disease, acne, psoriasis, actinomycosis, dysentery, biliary cirrhosis, Lyme disease, heat rash, Stevens-Johnson syndrome, mumps, pemphigus vulgaris, and blastomycosis. In certain other instances, methotrexate is used for the treatment of an autoimmune disease such as Type I diabetes mellitus, myasthenia gravis, vitiligo, Graves' disease, Hashimoto's disease, Addison's disease, autoimmune gastritis, autoimmune hepatitis, systemic lupus erythematosus, progressive systemic sclerosis and variants, polymyositis, dermatomyositis, pernicious anemia, primary biliary cirrhosis, autoimmune thrombocytopenia, Sjogren's syndrome, and multiple sclerosis.

As used herein, the term "arthritis" refers to an inflammatory condition that affects joints. Arthritis can be, for example, infective, autoimmune, or traumatic in origin, and includes, without limitation, acute arthritis, acute gouty arthritis, bacterial arthritis, chronic inflammatory arthritis, degenerative arthritis (osteoarthritis), infectious arthritis, juvenile arthritis, mycotic arthritis, neuropathic arthritis, polyarthritis, proliferative arthritis, psoriatic arthritis, juvenile rheumatoid arthritis, rheumatoid arthritis, venereal arthritis, and viral arthritis. In a preferred embodiment, the arthritis is rheumatoid arthritis. Rheumatoid arthritis is a chronic systemic disease primarily of the joints and is usually polyarticular, marked by inflammatory changes in the synovial membranes and articular structures and by muscle atrophy and rarefaction of the bones. Methotrexate is widely used in the treatment of rheumatoid arthritis, and one skilled in the art recognizes that the methods of the present invention can be practiced with a sample such as a cellular extract from a human or other mammal having rheumatoid arthritis or another form of arthritis.

In another embodiment, the present invention provides methods for determining a level of MTXPGs in an individual on MTX therapy or for optimizing dose efficacy of MTX therapy in an individual having cancer. For example, methotrexate is used for the treatment of a cancer such as lung cancer, breast cancer, bladder cancer, thyroid cancer, liver cancer, pleural cancer, pancreatic cancer, ovarian cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers; and osteogenic sarcomas, B-cell lymphoma, non-Hodgkin's lymphoma, Burkitt's lymphoma, fibrosarcoma, neuroblastoma, glioma, melanoma, monocytic leukemia, myelogenous leukemia, acute lymphocytic leukemia, and acute myelocytic leukemia.

C. Variant Alleles

The methods of the present invention rely on genotyping an individual to detect particular variant alleles, for example, at polymorphic sites in folate pathway genes such as RFC-1 and/or GGH. As used herein, the term "variant allele" refers to a stably heritable molecular variation that results in altered gene product levels or activity. Thus, a variant RFC-1 allele is a stably heritable molecular variation that results in altered RFC-1 levels or activity. Similarly, a variant GGH allele is a stably heritable molecular variation that results in altered GGH levels or activity.

Variant alleles useful in the present invention include, without limitation, single nucleotide polymorphisms (SNP), microsatellites (ms), variable number tandem repeat (VNTR) polymorphisms, and substitutions, insertions, or deletions of one or more nucleotides. One skilled in the art understands that a variant allele can also comprise a molecular variation such as abnormal methylation or other modification that does not produce a difference in the primary nucleotide sequence of the variant allele as compared to the wild-type allele.

The reduced folate carrier (RFC-1) is well known in the art and is described in, e.g., Matherly, *Prog. Nucl. Acid Res.*, 67:131-162 (2001)). The human RFC-1 coding sequence is available as Genbank accession AH006305, and genomic RFC-1 sequence is available under Genbank accessions U92873, U92872, U92871, U92870, U92869, and U92868.

A variant allele at a polymorphic site in an RFC-1 gene is located within the RFC-1 locus, which includes coding regions of the RFC-1 gene as well as non-coding regions such as introns and 5' and 3' untranslated regions. One skilled in the art understands that such a variant allele can be at a polymorphic site within, for example, the RFC-1 coding sequence, a promoter region 5' of the RFC-1 coding sequence, an enhancer region 5' or 3' of the RFC-1 coding sequence, an RFC-1 intronic sequence, or an mRNA stability region 3' of the RFC-1 coding sequence. In one embodiment, the variant allele at a polymorphic site in an RFC-1 gene is located within the RFC-1 coding sequence. In a preferred embodiment, the variant allele in the RFC-1 gene comprises a 80 G to A mutation in the RFC-1 coding sequence. However, one skilled in the art will appreciate that other RFC-1 variant alleles are also within the scope of the present invention.

In certain instances, a variant allele at a polymorphic site in an RFC-1 gene results in increased RFC-1 levels or activity. In certain other instances, a variant allele at a polymorphic site in an RFC-1 gene results in decreased RFC-1 levels or activity. Homozygosity, heterozygosity, or compound heterozygosity of such RFC-1 variant alleles can be associated with the level of MTXPGs in an individual, which in turn can be used to optimize the efficacy of MTX therapy. In a preferred embodiment, RFC-1 variant allele homozygosity is indicative of an increased level of MTXPGs in the individual relative to wild-type or heterozygous individuals. In another preferred embodiment, RFC-1 variant allele homozygosity is indicative of superior efficacy of methotrexate therapy in the individual.

The gamma glutamyl hydrolase (GGH) is known in the art and is described in, e.g., Yao et al., *Proc. Natl. Acad. Sci.*, 93:10134-10138 (1996)). The human GGH coding sequence is available as Genbank accession U55206.

A variant allele at a polymorphic site in a GGH gene is located within the GGH locus, which includes coding regions of the GGH gene as well as non-coding regions such as introns and 5' and 3' untranslated regions. One skilled in the art understands that such a variant allele can be at a polymorphic site within, for example, the GGH coding sequence, a promoter region 5' of the GGH coding sequence, an enhancer region 5' or 3' of the GGH coding sequence, a GGH intronic sequence, or an mRNA stability region 3' of the GGH coding sequence. In one embodiment, the variant allele at a polymorphic site in a GGH gene is located within the promoter region 5' of the GGH coding sequence. In a preferred embodiment, the variant allele in the GGH gene comprises a −401 C to T mutation in the GGH promoter. However, one skilled in the art will appreciate that other GGH variant alleles are also within the scope of the present invention.

In certain instances, a variant allele at a polymorphic site in a GGH gene results in increased GGH levels or activity. In certain other instances, a variant allele at a polymorphic site in a GGH gene results in decreased GGH levels or activity. Homozygosity, heterozygosity, or compound heterozygosity of such GGH variant alleles can be associated with the level of MTXPGs in an individual, which in turn can be used to optimize the efficacy of MTX therapy. In a preferred embodiment, GGH variant allele homozygosity is indicative of a decreased level of MTXPGs in the individual relative to wild-type or heterozygous individuals. In another preferred embodiment, GGH variant allele homozygosity is indicative of inferior efficacy of methotrexate therapy in the individual.

D. Methods of Genotyping

A variety of techniques can be used to genotype an individual at a polymorphic site in at least one folate pathway gene (e.g., RFC-1, GGH, etc.,) according to the methods of the present invention. For example, enzymatic amplification of nucleic acid from an individual can be conveniently used to obtain nucleic acid for subsequent analysis. However, the presence or absence of a variant allele in a folate pathway gene can also be determined directly from the individual's nucleic acid without enzymatic amplification.

Genotyping of nucleic acid from an individual, whether amplified or not, can be performed using any of various techniques known to one of skill in the art. Useful techniques include, without limitation, polymerase chain reaction (PCR)-based analysis, sequence analysis, array-based analysis, and electrophoretic analysis, which can be used alone or in combination. As used herein, the term "nucleic acid" means a polynucleotide such as a single- or double-stranded DNA or RNA molecule including, for example, genomic DNA, cDNA, and MRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix.

A sample containing nucleic acid can be routinely obtained from an individual. Such a sample refers to any biological matter from which nucleic acid can be prepared. As non-limiting examples, a sample can be whole blood, plasma, serum, saliva, cheek swab, or other bodily fluid, tissue, or extract that contains nucleic acid. In one embodiment, a method of the present invention is practiced with whole blood, which can be obtained readily by non-invasive means and used to prepare genomic DNA. In another embodiment, genotyping involves amplification of an individual's nucleic acid using the polymerase chain reaction (PCR). Use of PCR for the amplification of nucleic acids is well known in the art (see, e.g., Mullis et al. (Eds.), *The Polymerase Chain Reaction*, Birkhäuser, Boston, (1994)). In yet another embodiment, PCR amplification is performed using one or more fluorescently labeled primers. In a further embodiment, PCR amplification is performed using one or more labeled or unlabeled primers that contain a DNA minor grove binder.

Any of a variety of different primers can be used to amplify an individual's nucleic acid by PCR. For example, the PCR primers disclosed in Example 1 can be used to amplify the sequence surrounding a particular polymorphic site in RFC-1 or GGH. As understood by one skilled in the art, additional primers for PCR analysis can be designed based on the sequence flanking the polymorphic site(s) of interest. As a non-limiting example, a sequence primer can contain from about 15 to about 30 nucleotides of a sequence upstream or downstream of the polymorphic site of interest. Such primers generally are designed to have sufficient guanine and cytosine content to attain a high melting temperature which allows for a stable annealing step in the amplification reaction. Several computer programs, such as Primer Select, are available to aid in the design of PCR primers.

A Taqman® allelic discrimination assay available from Applied Biosystems can be useful for genotyping an individual at a polymorphic site and thereby determining the presence or absence of a variant allele. In a Taqman® allelic discrimination assay, a specific fluorescent dye-labeled probe for each allele is constructed. The probes contain different fluorescent reporter dyes such as FAM and VIC to differentiate amplification of each allele. In addition, each probe has a quencher dye at one end which quenches fluorescence by fluorescence resonance energy transfer. During PCR, each probe anneals specifically to complementary sequences in the nucleic acid from the subject. The 5' nuclease activity of Taq polymerase is used to cleave only probe that hybridizes to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Those skilled in the art understand that improved specificity in allelic discrimination assays can be achieved by conjugating a DNA minor grove binder (MGB) group to a DNA probe as described, e.g., in Kutyavin et al., *Nuc. Acids Research* 28:655-661 (2000). Minor grove binders include, but are not limited to, compounds such as dihydrocyclopyrroloindole tripeptide (DPI3).

Sequence analysis can also be useful for genotyping an individual at a polymorphic site. A variant allele can be detected by sequence analysis using the appropriate primers, which are designed based on the sequence flanking the polymorphic site of interest, as is known by those skilled in the art. As a non-limiting example, a sequence primer can contain from about 15 to about 30 nucleotides of a sequence that corresponds to a sequence about 40 to about 400 base pairs upstream or downstream of the polymorphic site of interest. Such primers are generally designed to have sufficient guanine and cytosine content to attain a high melting temperature which allows for a stable annealing step in the sequencing reaction.

The term "sequence analysis" refers to any manual or automated process by which the order of nucleotides in a nucleic acid is determined. As an example, sequence analysis can be used to determine the nucleotide sequence of a sample of DNA. The term sequence analysis encompasses, without limitation, chemical and enzymatic methods such as dideoxy enzymatic methods including, for example, Maxam-Gilbert and Sanger sequencing as well as variations thereof. The term sequence analysis further encompasses, but is not limited to, capillary array DNA sequencing, which relies on capillary electrophoresis and laser-induced fluorescence detection and can be performed using instruments such as the MegaBACE 1000 or ABI 3700. As additional non-limiting examples, the term sequence analysis encompasses thermal cycle sequencing (Sears et al., *Biotechniques* 13:626-633 (1992)); solid-phase sequencing (Zimmerman et al., *Methods Mol. Cell Biol.* 3:39-42 (1992); and sequencing with mass spectrometry, such as matrix-assisted laser desorption/ionization time-of-flight mass spectrometry (MALDI-TOF MS; Fu et al., Nature Biotech. 16:381-384 (1998)). The term sequence analysis further includes, but is not limited to, sequencing by hybridization (SBH), which relies on an array of all possible short oligonucleotides to identify a segment of sequence (Chee et al., *Science* 274:610-614 (1996); Drmanac et al., *Science* 260:1649-1652 (1993); and Drmanac et al., *Nature Biotech.* 16:54-58 (1998)). One skilled in the art understands that these and additional variations are encompassed by the term sequence analysis as defined herein.

Electrophoretic analysis can also be useful in genotyping an individual according to the methods of the present invention. "Electrophoretic analysis" as used herein in reference to one or more nucleic acids such as amplified fragments refers to a process whereby charged molecules are moved through a stationary medium under the influence of an electric field. Electrophoretic migration separates nucleic acids primarily on the basis of their charge, which is in proportion to their size, with smaller molecules migrating more quickly. The term electrophoretic analysis includes, without limitation, analysis using slab gel electrophoresis, such as agarose or polyacrylamide gel electrophoresis, or capillary electrophoresis. Capillary electrophoretic analysis generally occurs inside a small-diameter (50-100 m) quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs. Such methods of electrophoretic analysis, and variations thereof, are well known in the art, as described, for example, in Ausubel et al., *Current Protocols in Molecular Biology* Chapter 2 (Supplement 45) John Wiley & Sons, Inc. New York (1999).

Restriction fragment length polymorphism (RFLP) analysis can also be useful for genotyping an individual at a polymorphic site according to the methods of the present invention (Jarcho et al. in *Dracopoli* et al., *Current Protocols in Human Genetics* pages 2.7.1-2.7.5, John Wiley & Sons, New York; Innis et al.,(Ed.), *PCR Protocols*, San Diego: Academic Press, Inc. (1990)). As used herein, "RFLP analysis" refers to any method for distinguishing polymorphic alleles using a restriction enzyme, which is an endonuclease that catalyzes degradation of nucleic acid following recognition of a specific base sequence, generally a palindrome or inverted repeat. One skilled in the art understands that the use of RFLP analysis depends upon an enzyme that can differentiate a variant allele from a wild-type or other allele at a polymorphic site.

In addition, allele-specific oligonucleotide hybridization can be useful for genotyping an individual in the methods of the present invention. Allele-specific oligonucleotide hybridization is based on the use of a labeled oligonucleotide probe having a sequence perfectly complementary, for example, to the sequence encompassing the variant allele. Under appropriate conditions, the variant allele-specific probe hybridizes to a nucleic acid containing the variant allele but does not hybridize to the one or more other alleles, which have one or more nucleotide mismatches as compared to the probe. If desired, a second allele-specific oligonucleotide probe that matches an alternate (e.g., wild-type) allele can also be used. Similarly, the technique of allele-specific oligonucleotide amplification can be used to selectively amplify, for example, a variant allele by using an allele-specific oligonucleotide primer that is perfectly complementary to the nucleotide sequence of the variant allele but which has one or more mismatches as compared to other alleles (Mullis et al., supra). One skilled in the art understands that the one or more nucleotide mismatches that distinguish between the variant allele and other alleles are often located in the center of an allele-specific oligonucleotide primer to be used in the allele-specific oligonucleotide hybridization. In contrast, an allele-specific oligonucleotide primer to be used in PCR amplification generally contains the one or more nucleotide mismatches that distinguish between the variant and other alleles at the 3' end of the primer.

A heteroduplex mobility assay (HMA) is another well-known assay that can be used for genotyping at a polymorphic site in the methods of the present invention. HMA is useful for detecting the presence of a variant allele since a DNA duplex carrying a mismatch has reduced mobility in a polyacrylamide gel compared to the mobility of a perfectly base-paired duplex (Delwart et al., *Science,* 262:1257-1261 (1993); White et al., *Genomics,* 12:301-306 (1992)).

The technique of single strand conformational polymorphism (SSCP) can also be useful for genotyping at a polymorphic site in the methods of the present invention (see, e.g., Hayashi, *Methods Applic.,* 1:34-38 (1991)). This technique is used to detect variant alleles based on differences in the secondary structure of single-stranded DNA that produce an altered electrophoretic mobility upon non-denaturing gel electrophoresis. Variant alleles are detected by comparison of the electrophoretic pattern of the test fragment to corresponding standard fragments containing known alleles.

Denaturing gradient gel electrophoresis (DGGE) can be useful in the methods of the present invention. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in innis et al., supra, 1990).

Array-based methods for genotyping an individual at multiple polymorphic sites are particularly useful in the methods of the present invention. As used herein, the term "microarray" refers to an array of distinct nucleic acids (e.g., polynucleotides, oligonucleotides, etc.) synthesized on a substrate such as paper, membrane (e.g., nylon), filter, chip, glass slide, or any other suitable solid support. Microarrays typically comprise a plurality of different nucleic acid probes that are coupled to a surface of a substrate in different known locations. In certain instances, microarrays may be produced using mechanical synthesis methods as described in, e.g., U.S. Pat. No. 5,384,261. In certain other instances, microarrays may be produced using light directed synthesis methods which incorporate a combination of photolithographic methods and solid phase oligonucleotide synthesis methods as described in, e.g., Fodor et al., *Science* 251:767-777 (1991); U.S. Pat. Nos. 5,143,854 and 5,424,186.

Any of a variety of genotyping techniques using microarrays is within the scope of the present invention. In one embodiment, an individual is genotyped at one or more polymorphic sites using an oligonucleotide probe array. For example, U.S. Pat. No. 5,858,659 describes a method for analyzing polymorphic or biallelic markers using arrays of oligonucleotide probes that are capable of discriminating between the wild-type, heterozygous, and homozygous genotypes of genes of interest. In addition, U.S. patent Publication No. 20050042654 describes a method for analyzing single nucleotide polymorphic sites using arrays of allele-specific oligonucleotide probes. Other genotyping methods using oligonucleotide probe arrays are described in, e.g., U.S. Pat. Nos. 5,856,092, 6,300,063, 6,284,460, 6,361,947, and 6,368, 799; and U.S. patent Publication Nos. 20030186279, 20040146890, and 20050074787. In another embodiment, an individual is genotyped at one or more polymorphic sites using a polynucleotide probe array. For example, Flavell et al., *Nucl. Acids Res.* 31:e115 (2003), describes an array-based method for detecting single nucleotide polymorphisms using biotin-terminated allele-specific PCR products spotted onto streptavidin-coated glass slides and visualized by hybridization of fluorescent detector oligonucleotides to tags attached to the allele-specific PCR primers. In addition, Ji et al., *Mut. Res.* 548:97-105 (2004), describes an array-based method for detecting single nucleotide polymorphisms using amplified PCR products spotted onto glass slides which are then interrogated by hybridization with dual-color probes. One skilled in the art will know of additional methods for genotyping an individual at one or more polymorphic sites using oligonucleotide or polynucleotide probe arrays.

Other molecular methods useful for genotyping an individual at a polymorphic site are known in the art and useful in the methods of the present invention. Such well-known genotyping approaches include, without limitation, automated sequencing and RNase mismatch techniques (Winter et al., *Proc. Natl. Acad. Sci.*, 82:7575-7579 (1985)). Furthermore, one skilled in the art understands that, where the presence or absence of multiple variant alleles is to be determined, individual variant alleles can be detected by any combination of molecular methods. See, in general, Birren et al. (Eds.) *Genome Analysis: A Laboratory Manual* Volume 1 (Analyzing DNA) New York, Cold Spring Harbor Laboratory Press (1997). In addition, one skilled in the art understands that multiple variant alleles can be detected in individual reactions or in a single reaction (a "multiplex" assay).

In view of the above, one skilled in the art realizes that the methods of the present invention for determining a level of MTXPGs in an individual on methotrexate therapy or for optimizing dose efficacy of methotrexate therapy in an individual by genotyping the individual at a polymorphic site in at least one folate pathway gene can be practiced using one or any combination of the well-known techniques described above or other techniques known in the art.

IV. EXAMPLES

The following example is offered to illustrate, but not to limit, the claimed invention.

Example 1

Association Between Polymorphisms in the RFC-1 and GGH Genes and MTXPG Levels.

This example illustrates that common polymorphisms in the reduced folate carrier (RFC-1) and gamma glutamyl hydrolase (GGH) genes are predictive of the level of MTXPGs in an individual on methotrexate (MTX) therapy.

A. Patients and Methods
  1. Study Design

The study was cross-sectional at three investigational sites (The Center of Rheumatology, Albany, N.Y.; Rheumatology Practice, Knoxville, Tenn.; Radiant Research, Daytona Beach, Fla.). To be eligible, patients ($\geq 18$ yrs.) had to meet the revised criteria of the American Rheumatism Association for Rheumatoid Arthritis and had to have received low-dose MTX therapy for at least three months. Other medications included low-dose corticosteroids (<10 mg day) and folic acid supplementation for the prevention of side-effects induced by MTX. Local Institutional Review Board approved the study and patient consent was obtained for each patient. Patients' demographics were collected at the time of enrollment in the study. Blood was drawn in EDTA-containing tubes and shipped overnight to Prometheus Laboratories Inc. (San Diego, Calif.) for analysis.

2. HPLC Quantification of Red Blood Cell MTXPG Concentrations

Red blood cell MTXPG concentrations were measured as described previously using an HPLC-fluorometry procedure with a post-column photo-oxidation technique (Dervieux et al., *Clin. Chem.*, 49:1632-1641 (2003)). Results are expressed in nmol/L as either total $MTXPG_{1-5}$ levels or total long-chain $MTXG_{3-5}$ levels (i.e., the sum of $MTXP_3+MTXPG_4+MTXPG_5$ levels).

3. Genotyping Procedures

Genomic DNA was extracted using a Generation Purification Capture Column (Gentra Systems, Inc.; Minneapolis, Minn.) as per manufacturer instructions. Total genomic DNA was quantified using a Hitachi U-2000 spectrophotometer at 260 nm.

The RFC-1 G80A polymorphism (resulting in a histidine to arginine substitution at codon 27 of the RFC-1 gene) was detected using a PCR-RFLP method as previously described (Chango et al., *Mol. Genet. Metab.*, 70:310-315 (2000)). PCR amplification was performed with 5 ng genomic DNA in a final volume of 50 µl containing 900 nM forward primer (5'-AGT GTC ACC TTC GTC CCC TC-3'; SEQ ID NO:1), 900 nM reverse primer (5'-CTC CCG CGT GAA GTT CTT-3'; SEQ ID NO:2), and 1× AmpliTaq Gold master mix (Applied Biosystems; Foster City, Calif.). The PCR conditions consisted of a 5-minute initial denaturation at 95° C., followed by 35 cycles with denaturation for 15 seconds at 95° C., annealing/extension at 60° C., for 1 minute, with a final extension at 72° C., for 7 minutes. A 20 µl PCR product (amplicon of 230 bp) was subjected to enzymatic digestion at 37° C., using CfoI (Promega; Madison, Wis.) for 3 hours. Individuals with the RFC-1 80G/G wild-type genotype presented three fragments (125, 68, and 37 bp). Individuals with the RFC-1 80G/A heterozygous genotype presented 4 fragments (162, 125, 68, and 37 bp) and those with the RFC-1 80A/A homozygous genotype presented two fragments (162 and 68 bp).

The GGH −401CT promoter polymorphism was detected using a PCR-RFLP method as previously described (Chave et al., *Gene*, 319:167-175 (2003)). A total of 30 ng genomic DNA was amplified using the forward primer 5'-CGCTGC-CTGGTTACCAAACT-3' (SEQ ID NO:3) and the reverse primer 5'-TGTTACGTCGATGTGGACTTCAG-3' (SEQ ID NO:4) at a final concentration of 900 nM each in the presence of 1× AmpliTaqGold master mix. The PCR conditions consisted of a 5-minute initial denaturation at 95° C., followed by 40 cycles with denaturation for 15 seconds at 95° C., annealing/extension at 60° C., for 1 minute, with a final extension at 72° C., for 7 minutes. A 20 µl PCR product (amplicon of 109 bp) was subjected to enzymatic digestion at 55° C., using BslI (New England Biolabs; Berverly, Mass.) for 3 hours to overnight as appropriate. Individuals with the GGH −401C/C wild-type genotype presented one fragment (109 bp), individuals with the GGH −401C/T heterozygous genotype presented three fragments (109, 61, and 48 bp), and those with the GGH −401T/T homozygous genotype presented two fragments (61 and 48 bp).

4. Statistical Analyses

The statistical analysis consisted of a multivariate linear or logistic regression, with MTXPG levels (i.e., $MTXPG_{1-5}$, $MTXPG_{3-5}$) as dependent variables and predictors (i.e., age, weekly MTX dose, route of administration, and RFC-1 and GGH genotypes) as independent variables. For calculating a pharmacogenetic index, the genotypes were dichotomized as homozygous mutants (RFC-1 80A/A and GGH −401T/T; value of 1) versus wild-type or heterozygous (RFC-1 80G/G or 80G/A and GGH −401C/C or −401C/T; value of 0) as appropriate. Group comparisons were performed with the Kruskall-Wallis ANOVA. The likelihood of having MTXPG levels above group median was derived from the logistic regression model. Odds ratio (OR) and probability (P) are given with a 95% confidence interval (CI). Estimates are given with standard error.

B. Results

Figure 2:
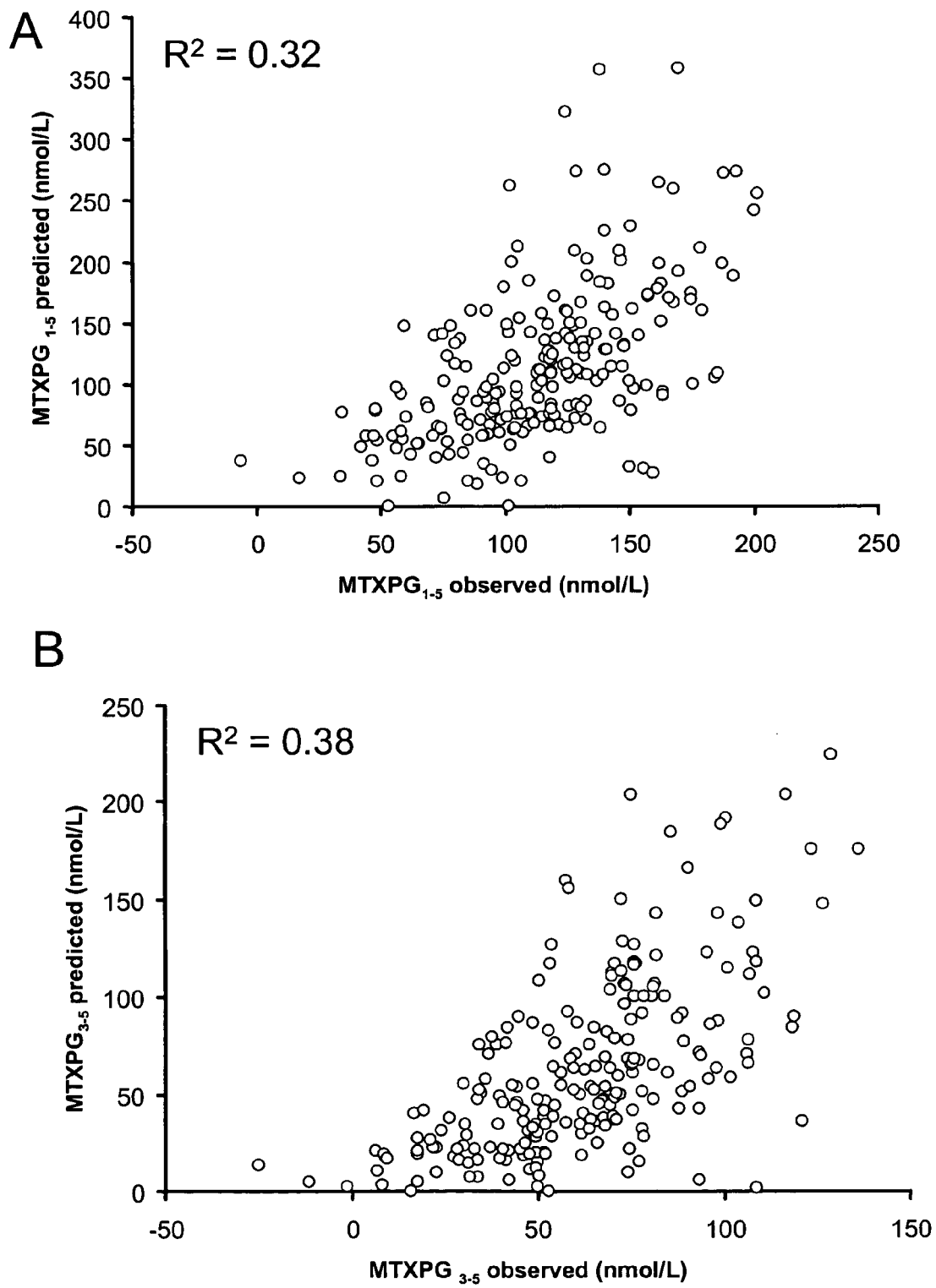
FIG. 2 shows a scatterplot of predicted versus observed MTXPG concentrations. MTXPG concentrations were predicted using a multivariate linear regression analysis including age, route of administration, weekly MTX dose, and RFC-1 and GGH genotypes according to the multivariate equation of Table 2.

A total of 226 patients who were undergoing MTX therapy for more than 3 months were enrolled from December 2002 to November 2003 at three different U.S. study sites. The median weekly MTX dose administered was 15 mg. A total of 184 patients (81%) received folic acid supplementation, and 107 patients (47%) were on concomitant low-dose corticosteroids. Median total $MTXPG_{1-5}$ level was 102 nmol/L and weekly dose of MTX ($p<0.001$), and route of administration ($p<0.04$) (see, Table 2). Older patients presented higher MTXPG concentrations while injected MTX resulted in higher MTXPG levels compared to oral administration. Although MTXPG levels were not significantly predicted by the number of RFC-1 80A alleles (estimate for $MTXPG_{1-5}=6.3\pm5.4$, $p=0.24$; estimate for $MTXPG_{3-5}=6.0\pm4.8$, $p=0.21$) or the number of GGH −401T alleles (estimate for $MTXPG_{1-5}=-3.7\pm3.4$, $p=0.31$; estimate for $MTXPG_{3-5}=-5.9=0.07$), homozygosity for RFC-1 80A/A, as compared to patients with the RFC-1 80G/G or 80G/A genotype, resulted in increased MTXPG levels ($p<0.033$), and homozygosity for GGH −401T/T, as compared to patients with the GGH −401C/C or −401C/T genotype, resulted in decreased MTXPG levels ($p<0.025$) (see, Table 2). Scatterplot analyses of predicted versus observed values for $MTXPG_{1-5}$ and $MTXPG_{3-5}$ concentrations are illustrated in FIG. 2A and FIG. 2B, respectively. Concurrent administration of folate and/or corticosteroids did not predict MTXPG levels ($p>0.70$).

TABLE 2

Multivariate Linear Regression of Red Blood Cell MTXPG Concentrations.

| | Global $R^2$ | Intercept | Age | MTX Dose | Route of Admin. | RFC-1 80A/A | GGH −401T/T |
|---|---|---|---|---|---|---|---|
| $MTXPG_{1-5}$ (nmol/L) | 0.32 | −103 ± 16 | 2.47 ± 0.29 $p < 0.001$ | 4.95 ± 0.78 $p < 0.001$ | 16.2 ± 8.0 $p = 0.04$ | 20.8 ± 9.7 $p = 0.033$ | −21.0 ± 9.6 $p = 0.029$ |
| $MTXPG_{3-5}$ (nmol/L) | 0.38 | −120 ± 24 | 1.53 ± 0.20 $p < 0.001$ | 4.39 ± 0.53 $p < 0.001$ | 15.6 ± 5.4 $p = 0.004$ | 14.8 ± 6.6 $p = 0.025$ | −15.3 ± 6.5 $p = 0.018$ |

Regression parameters for independent variables are provided for $MTXPG_{1-5}$ and $MTXPG_{3-5}$. The multivariate equation is as follows: MTXPGs (nmol/L) = intercept + ($\beta_1$ × Age) + ($\beta_2$ × Dose) + ($\beta_3$ × Route of Administration) + ($\beta_4$ × RFC-1 genotype) + ($\beta_5$ × GGH genotype). The independent variables are: age (in years), MTX dose (mg/week), route of MTX administration (0: oral; 1: injected); presence of the RFC-1 80A/A genotype (0: 80G/G or 80G/A; 1: 80A/A), and presence of the GGH −401T/T genotype (0: −401C/C or −401C/T; 1: −401T/T). Estimates ($\beta_n$) are given with SEM.

median long-chain $MTXPG_{3-5}$ level was 56 nmol/L. The allelic frequency was 43% for RFC-1 80A and 33% for GGH −401T. Patients' demographics are summarized in Table 1.

TABLE 1

Patients' Demographics.

| Parameter | Value |
|---|---|
| Age (yrs.) | 66 (26-91) |
| Time on MTX therapy (months) | 51 (3-279) |
| Weekly MTX dose (mg) | 15 (5-25) |
| Total MTXPG levels ($MTXPG_{1-5}$; nmol/L) | 102 (<5-358) |
| Total long-chain MTXPG levels ($MTXPG_{3-5}$; nmol/L) | 56 (<5-224) |
| RFC-1 G80A polymorphism | 80G/G n = 70 (31) |
| | 80G/A n = 121 (54) |
| | 80A/A n = 35 (15) |
| GGH-401CT polymorphism | −401C/C n = 112 (50) |
| | −401C/T n = 78 (35) |
| | −401T/T n = 36 (16) |

For the quantitative variables (age, time on MTX therapy, weekly MTX dose, total MTXPG levels, and total long-chain MTXPG levels), the median value is shown with the range of values in parenthesis. RFC-1 and GGH genotypes are expressed as the number (n) of individuals having a particular genotype with the corresponding percentage in parenthesis.

1. Multivariate Linear and Logistic Regression of MTXPG Concentrations

A multivariate linear regression analysis revealed that total $MTXPG_{1-5}$ and total long-chain $MTXPG_{3-5}$ levels were significantly and independently predicted by age ($p<0.001$), After adjustment for concomitant variables, patients with the GGH −401T/T genotype were 4.8-fold (OR CI 95% 1.8-13.0; $p=0.007$) more likely to have $MTXPG_{3-5}$ below group median as compared to patients with the GGH −401C/C or −401C/T genotype. Conversely, those with the RFC-1 80A/A genotype (OR CI 95% 1.4-8.4; $p<0.001$) were 3.4-fold more likely to have $MTXPG_{3-5}$ levels above group median as compared to those patients with the RFC-1 80G/G or 80G/A genotype.

2. A Pharmacogenetic Index for Determining MTXPG Levels

A pharmacogenetic index (PI) for determining MTXPG levels can be calculated as follows: (1) the RFC-1 gene is assigned a value of 1 when an RFC-1 80A/A homozygous genotype is present or a value of 0 when an RFC-1 80G/G wild-type genotype or RFC-1 80G/A heterozygous genotype is present; (2) the GGH gene is assigned a value of 1 when a GGH −401T/T homozygous genotype is present or a value of 0 when a GGH −401C/C wild-type genotype or GGH −401C/T heterozygous genotype is present; and (3) the value assigned to the GGH gene is subtracted from the value assigned to the RFC-1 gene (i.e., RFC-1 value−GGH value).

Because there was an opposite contribution of RFC-1 80A/A and GGH −401T/T variant allele homozygosity to intracellular MTXPG levels (estimates ~±15 for $MTXPG_{3-5}$, Table 2), patients with both RFC-1 80A/A and GGH −401T/T homozygous genotypes (5 patients) were combined with patients not having either homozygous genotype (160 patients). Under these conditions, a total of 31 patients presented an index of −1 (i.e., those with the GGH −401T/T homozygous genotype only), 165 patients presented an index of 0 (i.e., those not having either homozygous genotype or those with both homozygous genotypes), and 30 patients presented an index of 1 (i.e., those with the RFC-1 80A/A homozygous genotype only).

Figure 3:
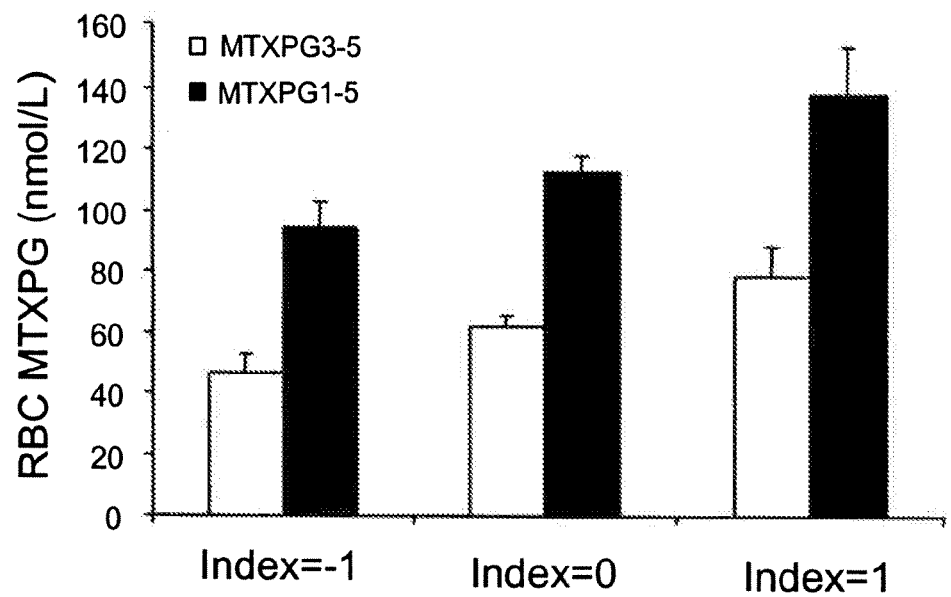
FIG. 3 shows the effect of the pharmacogenetic index (PI) on MTXPG concentrations. The PI was calculated as the presence of the RFC-1 80A/A genotype minus the presence of the GGH −401T/T genotype (see, Example 1).
Figure 3:
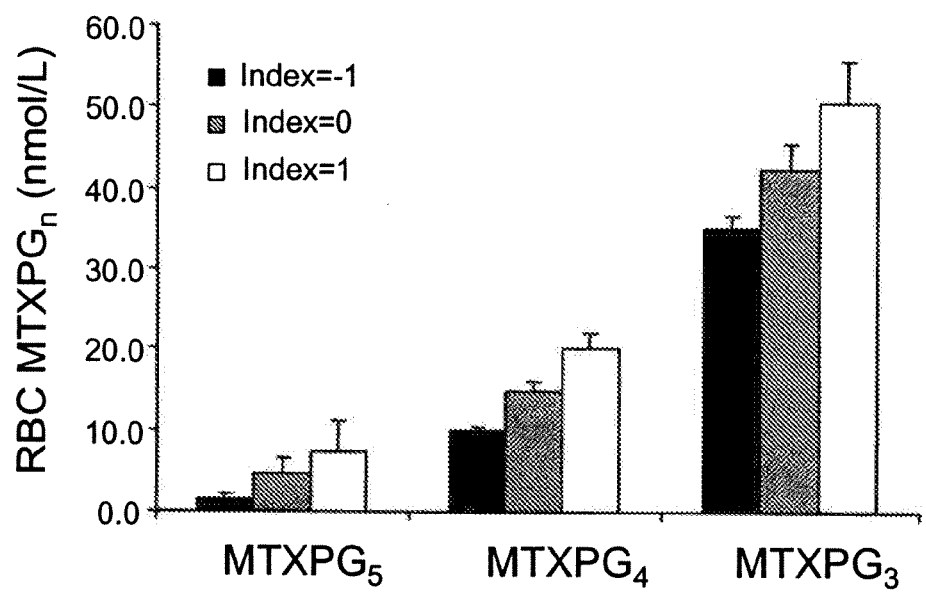

In an analysis without adjusting for age, dose, and route of administration, there was a significant relationship between increased PI value and increased intracellular MTXPG levels (Kruskall-Wallis; p<0.057) (FIG. 3A). Furthermore, increased PI was associated with increased $MTXPG_5$ levels (p<0.001), increased $MTXPG_4$ levels (p=0.035), and increased $MTXPG_3$ levels (p=0.027), although there were no significant differences in $MTXPG_2$ and MTXG, levels (p>0.70) (FIG. 3B). In a multivariate linear regression analysis adjusting for concomitance, the PI predicted significantly and independently $MTXPG_{1-5}$ (estimate=15.5±4.6; p=0.002; Global $R^2$=0.32) and $MTXPG_{3-5}$ (estimate=20.9±6.7; p=0.001; Global $R^2$=0.38) concentrations. Other estimates for intercept, age, MTX dose, and route of administration were similar to those presented in Table 2.

Figure 4:
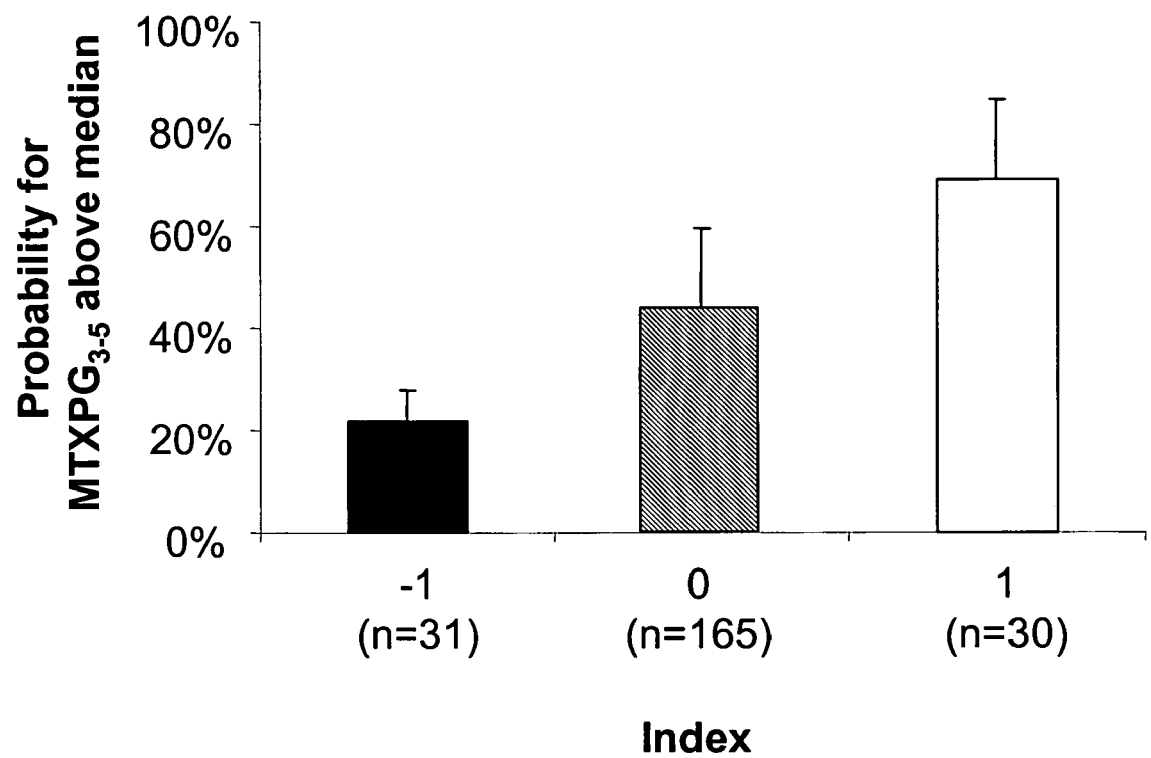
FIG. 4 shows the effect of the pharmacogenetic index (PI) on the probability for an individual to have MTXPG$_{3-5}$ levels above a median level. The equation for probability determination was: MTXPG$_{3-5}$ above median (0/1)=(−0.24±0.13)+(1.04±0.29×PI). Probabilities are given with standard error bars.

Finally, in a multivariate logistic regression analysis, there was a significant relationship between increased PI value and increased probability of $MTXPG_{3-5}$ levels above median (p<0.001). FIG. 4 illustrates the probability for a patient to have $MTXPG_{3-5}$ levels above median with respect to a given PI value.

C. Discussion

Several well-controlled clinical trials have demonstrated that MTX decreases functional disability with a maximum effect observable after 6 months of therapy. (Weinblatt et al., *N. Engl. J. Med.*, 312:818-822 (1985); Weinblatt et al., *Arthritis Rheum.*, 37:1492-1498 (1994)). However, recent findings from a large cohort of rheumatoid arthritis patients have surprisingly demonstrated that the time to maximize MTX effects is in fact longer that initially thought, thereby raising the concern that MTX dosage may be suboptimal (Ortendahl et al., *J. Rheumatol.*, 29:2084-2091 (2002)). Red blood cell (RBC) MTXPG levels have previously been shown to be associated with the therapeutic response to MTX, indicating that the routine monitoring of MTX therapy using MTXPG levels may provide utility to optimize therapy (Dervieux et al., *Arthritis Rheum.* 50:2766-2774 (2004)). The present study illustrates that common polymorphisms in RFC-1 and GGH were predictive of RBC MTXPG levels in vivo in large population of patients treated with low-dose MTX.

The present study was multi-centered with all patients undergoing MTX therapy for more than three months. A multivariate regression model was used to predict erythrocyte (i.e., RBC) MTXPG levels. For the analysis, age, MTX dose, route of administration, and RFC-1 and GGH genotypes were the independent variables. First, the analysis revealed that higher doses of MTX resulted in higher MTXPG levels. Second, injected MTX produced higher MTXPG levels compared to oral MTX, consistent with previous observations that injected MTX is associated with increased bioavailability compared to oral administration (Hamilton et al., *Br. J. Rheumatol.*, 36:86-90 (1997); Kumik et al., *Aliment. Pharmacol. Ther.*, 18:57-63 (2003)). However, the finding that older patients presented higher MTXPG levels should be carefully interpreted, as a decrease in MTX renal clearance in older patients may result in enhanced MTX bioavailability and thus enhanced intracellular MTXPG levels.

Recent evidences suggest that a G80A polymorphism in RFC-1 is associated with altered folate/anti-folate levels and modestly with the risk for a neural tube defect (Chango et al., *Mol. Genet. Metab.*, 70:310-315 (2000); Shaw et al., *Am. J. Med. Genet.*, 108:1-6 (2002); Morin et al., *Mol. Genet. Metab.*, 79:197-200 (2003)). Also, data suggest that individuals with the homozygous mutant RFC-1 80A/A genotype tend to have higher plasma folate and methotrexate levels (Laverdiere et al., *Blood*, 100:3832-3834 (2002); Chango et al., supra, (2000)) and higher red blood cell folate polyglutamate levels compared to those with the wild-type or heterozygous genotype (Shaw et al., supra, (2002)). This latter finding is consistent with the observation from the present study that RFC-1 80A/A homozygosity was predictive of increased MTXPG levels.

Previous in vitro data have demonstrated that a −401CT polymorphism in the GGH promoter is associated with increased luciferase activity, indicating that the polymorphism may result in increased GGH activity and increased MTXPG deconjugation (Chave et al., *Gene*, 319:167-175 (2003)). This finding is consistent with the observation from the present study that patients with the GGH −401T/T genotype presented decreased MTX polyglutamation compared to those with the −401C/C or −401C/T genotype. Because there was an opposite contribution of the RFC-1 80A/A and GGH −401T/T genotypes to MTXPG levels, a composite PI accounting for this dual effect was calculated, and patients with both RFC-1 80A/A and GGH −401T/T homozygous genotypes were combined with those having none of these homozygous genotypes. Under these conditions, the analysis revealed that the PI was strongly associated with MTXPG levels, supporting the notion that the sum of the contributions of individual genotypic components has the potential to maximize phenotypic expression in the context of low penetrance genetic polymorphisms.

Practically speaking, the PI of the present invention can be used to identify patients with a greater likelihood of success to MTX therapy (e.g., those with a PI of 1) and those requiring more aggressive MTX doses (e.g., those with a PI of −1). Of course, additional genetic markers in loci associated with MTX influx or efflux (e.g., multidrug resistance proteins (MRP)), polyglutamation (e.g., folylpolyglutamate synthetase (FPGS)), and/or catabolism (e.g., aldehyde oxidase) may also contribute to the pharmacokinetics of the drug (Ranganathan et al., *Ann. Rheum. Dis.*, 62:4-9 (2003); Zeng et al., *Cancer*, 61:7225-7232 (2001); Lee et al., *J. Natl. Cancer*, 92:1934-1940 (2000)).

In conclusion, the present study indicates that pharmacogenetic testing can be used to determine MTXPG levels and individualize MTX dose to maximize therapeutic effects.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for predicting a level of methotrexate polyglutamates 1 through 5 ($MTXPG_{1-5}$) in a human undergoing low dose methotrexate therapy, said method comprising:

genotyping said human for the presence of a gamma glutamyl hydrolase (GGH) −401T/T homozygous genotype; and predicting, based upon the presence of the GGH −401T/T homozygous genotype, a decreased level of $MTXPG_{1-5}$ relative to a human having a GGH −401C/T or C/C genotype.

2. The method of claim 1, wherein said human has an inflammatory disease, an autoimmune disease, or cancer.

3. The method of claim 2, wherein said inflammatory disease is rheumatoid arthritis.

4. The method of claim 1, wherein said genotyping is performed on genomic DNA.

5. The method of claim 4, wherein said genomic DNA is obtained from whole blood.

6. The method of claim 1, wherein said genotyping is performed using polymerase chain reaction (PCR) amplification followed by restriction fragment length polymorphism (RFLP) analysis.

7. The method of claim 1, wherein said method further comprises generating a pharmacogenetic index based upon the presence of said GGH −401T/T homozygous genotype.

8. The method of claim 7, wherein said pharmacogenetic index is indicative of the likelihood of success of said methotrexate therapy.

9. A method for predicting a level of methotrexate polyglutamates 3 through 5 ($MTXPG_{3-5}$) in a human undergoing low dose methotrexate therapy, said method comprising:

genotyping said human for the presence of a gamma glutamyl hydrolase (GGH) −401T/T homozygous genotype; and predicting, based upon the presence of the GGH −401T/T homozygous genotypes, a decreased level of $MTXPG_{3-5}$ relative to a human having a GGH −401 C/T or C/C genotype.

10. The method of claim 9, wherein said human has an inflammatory disease, an autoimmune disease, or cancer.

11. The method of claim 10, wherein said inflammatory disease is rheumatoid arthritis.

12. The method of claim 9, wherein said genotyping is performed on genomic DNA.

13. The method of claim 12, wherein said genomic DNA is obtained from whole blood.

14. The method of claim 9, wherein said genotyping is performed using polymerase chain reaction (PCR) amplification followed by restriction fragment length polymorphism (RFLP) analysis.

15. The method of claim 9, wherein said method further comprises generating a pharmacogenetic index based upon the presence of said GGH −401T/T homozygous genotype.

16. The method of claim 15, wherein said pharmacogenetic index is indicative of the likelihood of success of said methotrexate therapy.

17. The method of claim 1, wherein said human is receiving 5 mg to 25 mg of methotrexate per week.

18. The method of claim 1, wherein predicting said level of $MTXPG_{1-5}$ is based upon said genotype and at least one other factor selected from the group consisting of methotrexate dosage being taken by said human, route of administration of said methotrexate dosage, and age of said human.

19. The method of claim 9, wherein said human is receiving 5 mg to 25 mg of methotrexate per week.

20. The method of claim 9, wherein predicting said level of $MTXPG_{3-5}$ is based upon said genotype and at least one other factor selected from the group consisting of methotrexate dosage being taken by said human, route of administration of said methotrexate dosage, and age of said human.

* * * * *